United States Patent
Nelson et al.

(10) Patent No.: US 10,249,153 B2
(45) Date of Patent: Apr. 2, 2019

(54) WASTE CONTAINMENT APPARATUS AND METHOD FOR RECEIVING, ANALYZING, VERIFYING AND DISPOSING OF A CONTROLLED SUBSTANCE WASTE DOSE

(71) Applicant: Vigilant Waste Technologies, Inc., Austin, TX (US)

(72) Inventors: David A. Nelson, Austin, TX (US); Alfred Rafi Baddour, Austin, TX (US); Wayne J. Wehrer, Austin, TX (US)

(73) Assignee: Vigilant Waste Technologies, Inc., Austin, TX (US)

( * ) Notice: Subject to any disclaimer, the term of this patent is extended or adjusted under 35 U.S.C. 154(b) by 0 days.

(21) Appl. No.: 16/013,315

(22) Filed: Jun. 20, 2018

(65) Prior Publication Data

US 2018/0300994 A1 Oct. 18, 2018

Related U.S. Application Data

(62) Division of application No. 15/472,528, filed on Mar. 29, 2017, now Pat. No. 10,032,344.

(60) Provisional application No. 62/314,536, filed on Mar. 29, 2016.

(51) Int. Cl.
| | |
|---|---|
| *B65D 25/08* | (2006.01) |
| *G08B 5/36* | (2006.01) |
| *A61B 50/36* | (2016.01) |
| *A61K 9/00* | (2006.01) |
| *G01N 21/65* | (2006.01) |

(Continued)

(52) U.S. Cl.
CPC ............ *G08B 5/36* (2013.01); *A61B 50/36* (2016.02); *A61K 9/0019* (2013.01); *B65D 25/08* (2013.01); *G01N 21/65* (2013.01); *G01N 21/76* (2013.01); *G08B 21/18* (2013.01)

(58) Field of Classification Search
CPC ........ G08B 5/36; A61B 50/36; A61K 9/0019; B65D 25/08
USPC .......................................... 340/540; 220/501
See application file for complete search history.

(56) References Cited

U.S. PATENT DOCUMENTS

| | | |
|---|---|---|
| 6,868,344 B1 | 3/2005 | Nelson |
| 7,184,897 B2 | 2/2007 | Nelson |

(Continued)

*Primary Examiner* — John A Tweel, Jr.
(74) *Attorney, Agent, or Firm* — Egan Peterman Enders Huston

(57) ABSTRACT

Embodiments of waste containment apparatuses and methods are provided herein for receiving, analyzing, verifying and disposing of a controlled substance (CS) waste dose. One embodiment of a waste containment apparatus includes a plurality of single-dose containers, each having an inlet port for receiving a CS waste dose deposited within the single-dose container, an analysis chamber for reserving a fixed amount of the received CS waste dose for analysis, and a storage chamber for storing a remaining portion of the received CS waste dose. The waste containment apparatus includes further components for measuring a volume and determining a composition and concentration of the CS waste dose deposited within the single-dose container, and verifying the CS waste dose deposited within the single-dose container if the volume, composition and concentration of the CS waste matches information about the CS waste dose received from a depositor of the CS waste dose.

20 Claims, 13 Drawing Sheets

(51) Int. Cl.
*G08B 21/18* (2006.01)
*G01N 21/76* (2006.01)

(56) References Cited

U.S. PATENT DOCUMENTS

| | | |
|---|---|---|
| 7,458,741 B2 * | 12/2008 | Detwiler ................ A45D 34/04 |
| | | 401/132 |
| 8,195,328 B2 | 6/2012 | Mallett et al. |
| 8,684,968 B2 * | 4/2014 | Genosar ............ A61M 5/14248 |
| | | 604/132 |
| 9,302,134 B1 | 4/2016 | Nelson et al. |
| 9,456,958 B2 | 10/2016 | Reddy et al. |
| 9,796,526 B2 | 10/2017 | Smith et al. |
| 10,032,344 B2 * | 7/2018 | Nelson ..................... G08B 5/36 |
| 2017/0287290 A1 | 10/2017 | Nelson et al. |

* cited by examiner

WASTE CONTAINMENT APPARATUS AND METHOD FOR RECEIVING, ANALYZING, VERIFYING AND DISPOSING OF A CONTROLLED SUBSTANCE WASTE DOSE

This application is a divisional application of U.S. application Ser. No. 15/472,528 filed Mar. 29, 2017 and claims priority to Provisional Patent Application No. 62/314,536 filed Mar. 29, 2016.

BACKGROUND OF THE INVENTION

1. Field of the Invention

The invention relates generally to the disposal of controlled substances. Specifically, the invention relates to systems, apparatuses and methods for disposing and documenting the disposal of controlled substances. More specifically, the invention relates to automatically verifying, tracking and securing all injectable, post-patient controlled substance waste.

2. Description of the Related Art

The following descriptions and examples are not admitted to be prior art by virtue of their inclusion within this section.

The Comprehensive Drug Abuse Prevention and Control Act of 1970 and the Controlled Substance Import and Export Act are collectively referred to as the Controlled Substances Act (CSA). The CSA is implemented and enforced by the Drug Enforcement Agency (DEA) with the purpose to prevent, detect and eliminate the diversion of controlled substances and listed chemicals for illicit uses while maintaining an adequate supply of these materials for legitimate uses in areas of medicine, scientific research, and industry. The CSA requires the DEA to maintain a system for monitoring the manufacture, distribution, dispensing, importation and exportation of controlled substances. For those entities (e.g., hospitals, long-term care facilities, pharmacies, etc.) that are registered to possess controlled substances with the DEA, the regulations regarding the handling, distribution, and destruction of controlled substances are well defined in the requirements of their registration.

A controlled substance is a drug or drug product that comes under the jurisdiction of the Controlled Substances Act of 1970 including, but not limited to narcotics, depressants, stimulants, hallucinogenic and anabolic steroid drugs. Controlled substances are considered to be dangerous by the DEA and require direct physician supervision for administration. Examples of controlled substances include, but are not limited to, hydromorphone hydrochloride (HCL), fentanyl citrate, morphine sulfate, phenobarbitol, meperidine, midazolam, midazolam HCL, propofol, lorazepam, hydrocondone/acetaminophen, remifentanil HCL, sufentanil citrate, butorphanol tartrate, fentanyl 2 mcg/ml with bupivicaine 0.125% epidural solution, ketamine HCL, fentanyl/sodium chloride, diazepam, hydrocodone/clorpheneramine, lacosamide, morphine and alfentanil HCL.

A controlled substance may be obtained in a variety of ways by licensed facilities, pharmacies, and caregivers. For instance, a controlled substance may be dispensed by the manufacturer or pharmaceutical supplier directly to the healthcare facility (i.e., hospital, laboratory, or patient care facility) or pharmacy. In addition, a healthcare facility or pharmacy may directly dispense the controlled substance in a unit dose or as part of a drug pack, which may include varying amounts of controlled drugs. Furthermore, a healthcare facility or pharmacy may dispense a controlled substance through an automated drug dispensing machine (ADM), such as those manufactured by Omnicell® (Mountain View, Calif.) or Pyxis® (San Diego, Calif.).

Once a controlled substance is obtained, it may be administered to a patient, utilized as part of an infusion, or utilized in a laboratory study. However, there is often an excess of the drug that must be disposed of in a controlled manner, as regulated by enforcement agencies such as the DEA, State Boards of Pharmacy, and state and local law enforcement agencies. Failure to adhere to their regulations can bring stiff penalties such as fines, imprisonment, and loss of license to handle and dispense controlled substances. Because of this, it is imperative for anyone involved in the use of controlled substances to strictly follow these regulations.

Policies of regulatory agencies and patient care facilities dictate that any excess drug be disposed and rendered useless for human consumption. Although there is a need for properly disposing of all controlled substances, the need is particularly relevant to injectable controlled substances. For instance, hospitals and other healthcare facilities typically dispense injectable controlled substances in patient-specific "one-size-fits-all" vials, yet often times administer only a portion of the contents to the patient. The remaining contents must be disposed of in a manner, which is tightly regulated by the States and Drug Enforcement Agency so as to prevent diversion of narcotics for illicit use. The DEA recently transferred a substantial portion of the regulatory burden to the States and other local enforcement bodies for the documentation and verification requirements for disposing of post-patient controlled substance waste. Hospitals may now risk compliance violations, as well as continuing escalation of drug diversion, as they work to comply with the shifting regulatory landscape. As a result of the regulatory documentation requirements, an industry was born to effectively distribute, document and track the utilization of these drugs.

There are three major components to satisfying the Controlled Substance Act of 1970, including tracking and documenting the distribution, utilization and disposal of controlled substances. While there are commercially available systems for tracking and documenting the distribution and utilization of controlled substances, the last component is the disposal (or "wasting") process, which remains a manual process and is equally prone to abuse, diversion and a host of regulatory and efficiency concerns.

In the absence of technology to assist with controlled substance wastage, medical care providers are required to manually document, countersign and track the heavily regulated process. More frequently than not, there is excess drug during routine administration that must be disposed of under strict guidelines overseen by the DEA, State Boards of Pharmacy and state and local law enforcement agencies. The guidelines require:

Excess drug from routine administration be disposed of and rendered unusable for human consumption;

The wastage process must be witnessed and countersigned by licensed personnel;

The witness must visually observe the identity, quantity and disposal of the controlled substance, attesting to the process via handwritten signature or electronic password; and The wastage process must be documented with the overseeing authority, which then must reconcile the medication administration record with the wastage record.

The disposal or "wasting" process typically used in a hospital or patient care facility is imperfect. Typically, a controlled substance is disposed of by injection into a sink, expelled onto the floor, or dropped into a needle disposal container. In the case of partially used vials of controlled substances, these are sometimes deposited intact into needle disposal containers and could potentially be retrieved for unauthorized or illicit use. The current disposal methods also present a compliance dilemma in states, such as California, where Schedule II waste is required to be collected for incineration.

Once the controlled substance is wasted, the process must be documented. To document the wastage, the person wasting the controlled substance must find another person to witness the waste process and verify the process by way of a handwritten signature or an electronic password on a computerized system, such as the Omnicell® or Pyxis® system mentioned above. In most facilities, this requires the signature of a person with an advanced clinical degree, such as a Registered Nurse or an authorized clinician. During busy times, this process may be delayed or forgotten.

Documentation typically consists of recording information, such as the patient's name, the name of the controlled substance and its concentration, and the quantity (e.g., volume) that is wasted. Frequently, waste transaction records are handwritten and therefore prone to the pitfalls of poor handwriting and illegibility during review. Other times, waste transaction records are generated through computerized dispensing system units, such as the Omnicell® or Pyxis®. These systems require both the person wasting the substance (the "controlled substance possessor") and the witness to log on and complete several screen commands to complete the wasting/documentation process. Once documentation is complete, the record of the controlled substance administration (i.e., the patient's record) must match the waste transaction record. This is a labor-intensive task that requires a pharmacy's staff to spend hours reviewing records and reconciling discrepancies that arise during reviews.

There are several serious shortcomings of the current disposal system and method. Firstly, all injectable controlled substances are currently manufactured as clear liquids, meaning their appearance is the same as saline or even water. This creates the potential for easily substituting any other clear liquid for the controlled substance. The potential for theft of these drugs for self-medication or illicit sale remains high even with the strictest enforcement. Furthermore, as the current disposal process is primarily manual and adjudicated by the same individuals that are being monitored, it is riddled with inefficiency, opportunity for diversion and theft, compromised by increasing time restraints and creates conflict among those responsible for administration. Therefore, a need exists for a system, apparatus and method for accurately and automatically verifying, tracking and securing all post-patient controlled substance waste.

SUMMARY OF THE INVENTION

Embodiments of waste containment apparatuses and methods are provided for receiving, analyzing, verifying and disposing of controlled substances. The following description of various embodiments of methods and apparatuses is not to be construed in any way as limiting the subject matter of the appended claims.

According to one embodiment, a waste containment apparatus is provided herein comprising a plurality of single-dose containers, each configured for receiving a controlled substance waste dose, and a collector configured for holding the plurality of single-dose containers for secure containment within the waste containment apparatus. In general, each single-dose container may comprise an inlet port for receiving a controlled substance waste dose, an analysis chamber coupled to the inlet port for receiving and reserving a fixed amount of the received controlled substance waste dose for analysis, and a storage chamber coupled to the analysis chamber for receiving and storing a remaining portion of the received controlled substance waste dose. In some embodiments, the inlet port may be substituted with a simple opening in the analysis chamber allowing direct line-of-sight to the top surface of the fluid pool in the analysis chamber at a direction roughly perpendicular to this surface.

In some embodiments, each single-dose container may further comprise a spillway arranged near a top of the analysis chamber to provide an outlet for the remaining portion of the received controlled substance waste dose to spill over into the storage chamber. In some embodiments, the analysis chamber may be configured for reserving about 0.1 ml to about 2 ml of the received controlled substance waste dose, and the storage chamber may be configured for storing about 5 ml to about 20 ml of the received controlled substance waste dose.

In some embodiments, the analysis chamber and/or the storage chamber comprise an optically transmissive material to facilitate waste analysis within the analysis chamber and/or volumetric measurements within the storage chamber of the single-dose container. It is noted, however, that analysis chamber and/or the storage chamber may be formed from an optically opaque material if optical transparency is not required for the analysis or measurement procedures. In some embodiments, the analysis chamber may be internally lined with a reflective material to facilitate analysis by optical means. In some embodiments, the waste containment apparatus may further include an analyzer, which may be coupled to the analysis chamber for determining at least one of a volume, composition and/or concentration of the controlled substance waste dose reserved within the analysis chamber. Although not limited to such, the analyzer may be configured for determining a composition and/or concentration of the controlled substance waste dose using a Rayleigh scattering or a Raman spectroscopy technique. In other embodiments, the waste containment apparatus may include a laser level, a camera or a flowmeter, which is coupled to detect an amount or volume of the controlled substance waste dose received within the single-dose container.

In some embodiments, each single-dose container may further include a second inlet port for receiving another substance into the analysis chamber and/or the storage chamber. For example, the second inlet port may be used to introduce nanoparticles into the analysis chamber for the purpose of enhancing certain analysis techniques. In some embodiments, the second inlet port may be used to introduce an agent into the analysis and storage chambers, which may function to denature, adulterate, destroy, neutralize and/or disinfect the controlled substance contained therein to render it non-infectious and/or unusable for human consumption. In some embodiments, each single-dose container may further include a cap, which when closed, is configured for engaging with and sealing the first inlet port and/or the second inlet port. The cap may be closed to ensure that a controlled substance waste dose is secured within the single-dose container for transport and/or to ensure that a fixed amount of the controlled substance remains in the analysis chamber during certain analytical techniques (e.g., Raman spectroscopy).

In some embodiments, the waste containment apparatus may further comprise one or more input devices and an information reconciler and recorder. The one or more input devices may be generally configured for receiving information specific to each controlled substance waste dose deposited into the waste containment apparatus and received within each single-dose container. The information reconciler and recorder may be securely disposed within a housing of the waste containment apparatus. As used herein, "securely disposed" means that unauthorized access to the information reconciler and recorder is prevented, e.g., by a locking mechanism provided on the housing. The information reconciler and recorder may be configured for comparing the composition, concentration and/or volume of the controlled substance waste dose identified by the analyzer to the information received via the one or more input devices to determine if a match exists, and for producing a comparison result indicative of a confirmed match or an unconfirmed match based on said comparing. In some embodiments, the information reconciler and recorder may be further configured for generating a waste transaction record comprising the identification results, the received information and the comparison results for each controlled substance waste dose.

According to another embodiment, a method is provided herein for receiving, analyzing, verifying and disposing of a controlled substance waste dose. In general, the method may include receiving a controlled substance waste dose deposited within a single-dose container securely disposed within a waste containment apparatus. After the controlled substance waste dose is received, the method may include measuring a volume of the controlled substance waste dose deposited within the single-dose container, determining a composition and concentration of the controlled substance waste dose deposited within the single-dose container and comparing the volume, composition and concentration of the controlled substance waste to information pertaining to the controlled substance waste dose. The information pertaining to the controlled substance waste dose may be received, for example, via an input device of the waste containment apparatus from a depositor of the controlled substance waste dose. In some embodiments, the method may include verifying the controlled substance waste dose deposited within the single-dose container if the comparison step determines that the volume, composition and concentration of the controlled substance waste deposited within the single-dose container matches the received information pertaining to the controlled substance waste dose.

In some embodiments, the method may include receiving the information pertaining to the controlled substance waste dose. The received information may include, for example, a National Drug Code (NDC) number, a drug type, a concentration and/or an original volume of the controlled substance prior to administration to a patient. In some embodiments, the information may be received by scanning a barcode on a container originally containing the controlled substance waste dose to obtain the information pertaining to the controlled substance waste dose.

In some embodiments, the volume of the controlled substance waste dose deposited within the single-dose container may be measured using a laser level, a weight measurement, a camera site level reading or a flowmeter. In some embodiments, the composition and concentration of the controlled substance waste dose deposited within the single-dose container may be determined using a Rayleigh scattering or a Raman spectroscopy technique.

In some embodiments, the method may include sequestering the controlled substance waste dose within the single-dose container in its original form if the comparison step determines that the volume, composition and/or concentration of the controlled substance waste dose does not match the received information pertaining to the controlled substance waste dose.

In other embodiments, if the comparing step determines that the volume, composition and/or concentration of the controlled substance waste dose matches the received information pertaining to the controlled substance waste dose, the method may further include rendering the controlled substance waste dose unusable for human consumption by adding an agent and/or an absorbent material to the controlled substance waste dose deposited within a single-dose container. In some embodiments, the controlled substance waste dose may be rendered unusable for human consumption by adding the agent and/or the absorbent material into the single-dose container.

In other embodiments, the controlled substance waste dose may be rendered unusable for human consumption by depositing the controlled substance waste dose into a waste storage bin securely disposed within the waste containment apparatus, and introducing an absorbent material into the waste storage bin after the controlled substance waste dose is deposited into the waste storage bin to render the controlled substance waste dose unusable, irretrievable and/or in a form suitable for non-regulated waste disposal. In some embodiments, the absorbent material may be introduced into the waste storage bin after the controlled substance waste dose is deposited into the waste storage bin. In other embodiments, the absorbent material may be introduced into the waste storage bin after multiple controlled substance waste doses from a plurality of single-dose containers are deposited into the waste storage bin.

BRIEF DESCRIPTION OF THE DRAWINGS

For a more complete understanding of the present invention, and the advantages thereof, reference is now made to the following descriptions taken in conjunction with the accompanying drawings, in which.

Figure 1:
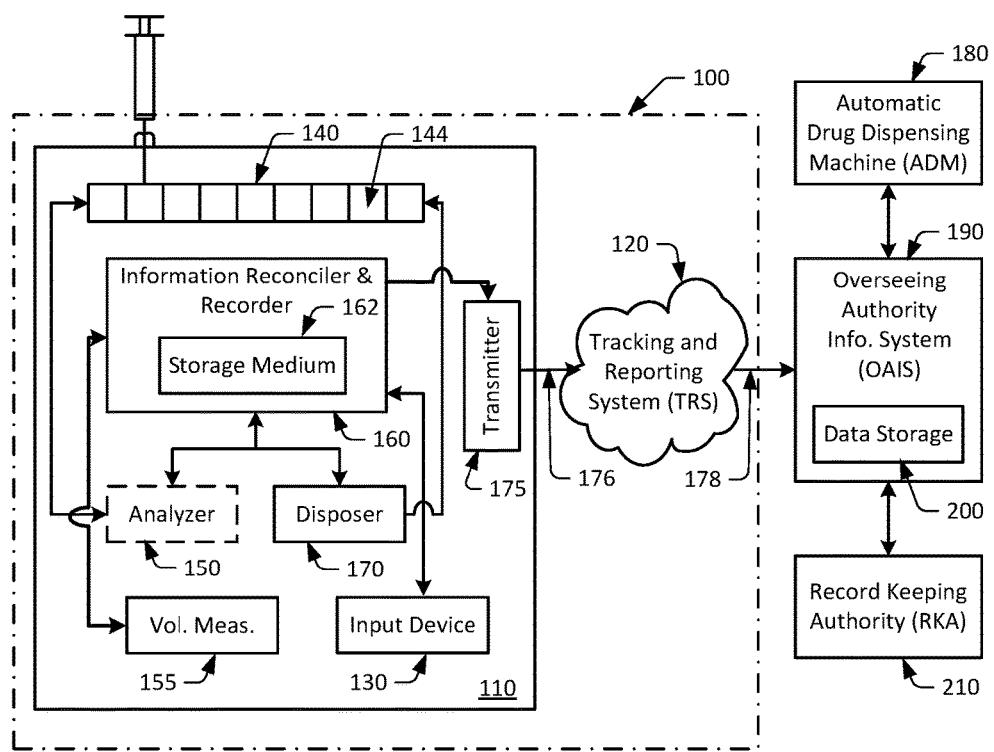
FIG. 1 is a block diagram of a controlled substance waste tracking and disposal system comprising a waste containment apparatus and a tracking and reporting system.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE INVENTION

Reducing drug diversion in hospitals and other patient-care facilities is a compliance challenge, which has become important to the well-being of patients and caregivers. The expected onset of new DEA rules and the continuing epidemic of prescription drug abuse in America are driving the urgency for improved control in the hospital waste stream of controlled substances. In response, the present inventors have created an integrated system, apparatus and methods for properly tracking, verifying, and documenting waste disposal in a way, which is compatible with the healthcare facility workflow. According to one embodiment, the system, apparatus and methods described herein may automatically verify, track, document and secure all injectable Schedule II post-patient controlled substance (CS) waste. Expected benefits include improved compliance, higher efficiency, reduced diversion, and lower labor costs.

The system, apparatus and methods described herein provide immediate detection of drug diversion and fraud, and enable full compliance with all current laws and rules, including new DEA regulations. Reduced diversion improves patient care by providing more patients the medication they need, while providing fewer opportunities for clinicians to become drug-impaired and threaten patient safety. The apparatus described herein also uniquely addresses a compliance dilemma presented in section 1304.22(e)(3)(iii) of the new DEA rules (formerly 1317.25 (b)(2)(iii) of the proposed DEA rules) resulting from the Secure and Responsible Disposal Act of 2010 specific to the transfer of custody between DEA registrants which states:

"For controlled substances in a . . . receptacle that has been opened: If the substance is listed in Schedule I or II, make an exact count or measure of the contents . . . "

The apparatus described herein enables full compliance with this rule by sequestering each discrepant controlled substance waste dose in its own bar coded single-dose container and creating an electronic waste transaction record of the disposal. This allows for full traceability of each individual waste dose. When optionally equipped with an on-board analyzer, the apparatus can replace the human witness required in the current waste disposal process by automatically verifying the composition, concentration, and volume of each waste dose. Notably, a human witness is completely incapable of verifying the composition and concentration of waste drugs.

The system, apparatus and methods described herein integrate well into the workflow of the hospital and pharmacy to improve both the operational efficiency and the cost efficiency of the waste disposal process. For example, the apparatus described herein offloads the low-value repetitive tasks typically associated with wasting drugs from the pharmacist and other clinicians, and performs these tasks more accurately and with better record keeping than current manual processes. This may allow pharmacists to focus more attention on recommending and directing patient-specific therapies in consultations with the attending physicians, and allow the clinicians to focus more on direct patient care. Since the apparatus eliminates the need for a human witness when equipped with the on-board analyzer, an immediate 50% reduction in labor associated with witnessed drug wasting should be realized by the hospital or patient-care facility.

According to some embodiments, the apparatus described herein may perform these major tasks:
  Secures waste with full traceability by dose
  Provides real-time cloud-based tracking and reporting
  Automatically verifies waste drug composition and volume when equipped with the optional on-board analyzer
  Adulterates waste when equipped with the optional adulterant container In doing so, the apparatus may provide the following benefits to hospitals and other patient care facilities:
  Full compliance with all state and federal laws
  Immediate diversion detection
  Full traceability by individual dose
  Non-infectious safe disposal
  Enhanced patient safety
  Reduced labor costs It is noted that although the disclosed system, apparatus and methods are provided for automatically verifying, tracking, securing and disposing of all injectable Schedule II post-patient controlled substance (CS) waste, they are not strictly limited to Schedule II CS waste, injectable CS waste, or controlled substances administered to patients. In some embodiments, the disclosed system, apparatus and methods may be used for automatically verifying, tracking, securing and disposing of non-drug controlled substances, such as controlled chemicals or biologically hazardous materials.

Turning now to the drawings, FIG. 1 is a block diagram illustrating one embodiment of a controlled substance waste tracking and disposal system 100 comprising at least one waste containment apparatus (WCA) 110 and a tracking and reporting system (TRS) 120. As described in more detail below, waste containment apparatus 110 may generate a waste transaction record for every controlled substance waste dose secured/disposed within the apparatus 110. In some embodiments, the waste transaction records generated for each CS waste dose deposited within the waste containment apparatus 110 may be stored within a storage medium of the WCA 110. In one example, the waste transaction records may be stored within a storage medium of information reconciler and recorder 160.

As shown in FIG. 1, waste containment apparatus 110 is operably coupled to the tracking and reporting system 120 for transmitting waste transaction records to the tracking and reporting system 120. In some embodiments, a plurality of waste containment apparatuses 110 may be included within system 100, each operably coupled to the tracking and reporting system 120 for transmitting waste transaction records there to. In some embodiments, tracking and reporting system 120 may comprise a storage medium for storing the waste transaction records received by one or more waste containment apparatuses 110.

As used herein, the term "operatively coupled" means connected in such a way that data may be exchanged. It is understood that "operatively coupled" does not require a direct connection, a wired connection, or even a permanent connection. It is sufficient for purposes of the present disclosure that connection(s) 176 between the waste containment apparatus(es) 110 and the tracking and reporting system 120 be established for the sole purpose of exchanging information. The connection 176 may be across a network, the Internet, an intranet, or dedicated lines, and may otherwise be referred to as a "communication link." As such, the waste containment apparatus(es) 110 may each comprise a transmitter 175 for transmitting the waste transaction records over the communication link to the tracking and reporting system 120. In some embodiments, the waste containment apparatus(es) 110 may comprise a transceiver, instead of a transmitter, for also receiving data from the tracking and reporting system 120 over the communication link, as discussed in more detail below.

Although not limited to such placement, the waste containment apparatus(es) 110 may be placed in a patient care area (e.g., an emergency room, operating room or intensive care unit) of a hospital or other patient-care facility for convenient containment and/or disposal of post-patient controlled substance waste doses. Although described herein for the disposal of Schedule II controlled substance liquid injectables, the waste containment apparatus(es) 110 may be additionally configured for securing/disposing of other forms of controlled substances including, but not limited to, a solid form such as a pill or tablet, a liquid form still in a vial or syringe, an aerosol form, or a patch form. Example embodiments of apparatuses configured for securing/disposing other forms of controlled substances are described in commonly assigned U.S. Pat. Nos. 6,868,344, 7,184,897 and 9,302,134, each of which are incorporated herein in their entirety.

Waste containment apparatus 110 may be operated by an individual possessing a controlled substance (i.e., a "controlled substance possessor"), which in most cases, will be the clinician or nurse who obtained and/or administered a portion of the controlled substance to the patient. According to one embodiment, a controlled substance possessor may obtain a controlled substance dose from an automatic drug dispensing machine (ADM) 180, such as the Omnicell® or Pyxis® system mentioned above. As described in more detail below with respect to FIG. 20, ADM 180 may generate a dispenser transaction report for each controlled substance dose dispensed by the ADM. As shown in FIG. 1, ADM 180 may be operably coupled to an overseeing authority information system (OATS) 190 for transmitting and optionally storing the dispenser transaction reports within a data storage medium 200 of the OAIS 190. The OAIS 190 is a centralized system for storing and processing information. Information stored within a data storage medium 200 of the OAIS 190 may include for example, a patient's Medication Administration Report (MAR), a pharmacy report of medications, an anesthesia record, records from ADM 180, and other types of data collectively referred to herein as "hospital records."

As shown in FIG. 1, the tracking and reporting system 120 may also be operably coupled to the OAIS 190 via another communication link. As described in more detail below with respect to FIGS. 11 and 14, a record keeping authority 210 (e.g., a pharmacist, charge nurse or other responsible personnel) may access the waste transaction records stored within the tracking and reporting system 120 and the hospital records stored within the OAIS 190 for reconciling the waste transaction records with corresponding hospital records.

Figure 2:
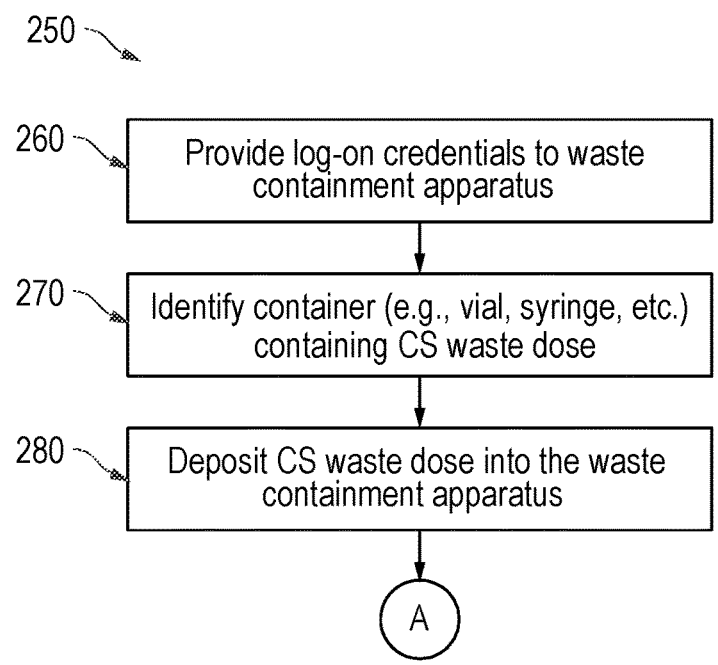
FIG. 2 is a flowchart diagram illustrating an embodiment of a method, which is performed by a controlled substance (CS) possessor for disposing of a controlled substance within a waste containment apparatus.
Figure 3:
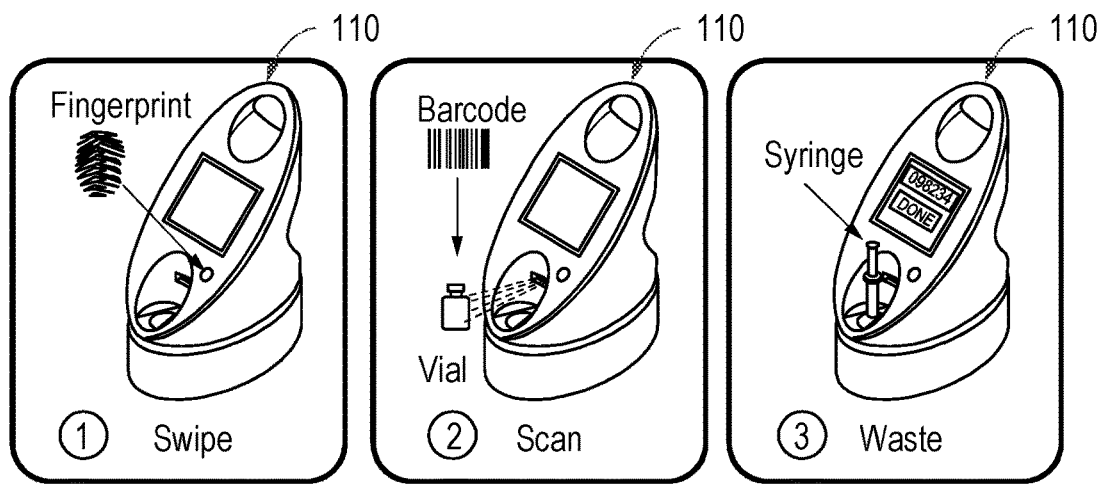
FIG. 3 is a pictorial diagram illustrating one embodiment of the method shown in FIG. 2 and provides a perspective view of the waste containment apparatus of FIG. 1, according to one embodiment.

FIG. 2 is a flowchart diagram illustrating one embodiment of a method 250, which may be performed by a controlled substance possessor for securing/disposing of a controlled substance (CS) waste dose (i.e., the portion of the controlled substance not administered to the patient) within the waste containment apparatus 110. FIG. 3 is a pictorial diagram illustrating one embodiment of the method 250 shown in FIG. 2 and provides a perspective view of the waste containment apparatus 110 of FIG. 1, according to one embodiment.

In one embodiment, method 250 may begin when a controlled substance possessor (e.g., a registered nurse or clinician) provides log-on credentials in step 260 to log-on to the waste containment apparatus 110. Although not limited to such, log-on credentials may be provided to the WCA 110 via a finger print swipe or scan, as shown in the exemplary embodiment of FIG. 3. Alternatively, log-on credentials may be provided to the WCA 110 via other biometric sensor(s), a password entry or a barcode scan of an identification card. In step 270, the controlled substance possessor identifies the container (e.g., the vial, syringe, etc.) originally or currently containing the CS waste dose to the waste containment apparatus 110. According to one embodiment, the container may be identified in step 270 by scanning a barcode on the container to provide information pertaining to the CS waste dose, as shown in FIG. 3. Such information may include, but is not limited to, a National Drug Code (NDC) number, drug type, concentration and original volume of the controlled substance prior to administration. In step 280, the controlled substance possessor deposits the CS waste dose into the waste containment apparatus 110 to securely contain the waste dose therein. For example, an injectable waste dose may be deposited into the waste containment apparatus 110 by using a syringe to inject the waste dose into the apparatus, as shown in FIG. 3. Other means for depositing the CS waste dose into the apparatus may also be used, depending on the form of the waste dose. All subsequent steps of measuring, analyzing, adulterating, verifying and reporting are performed automatically by the waste containment apparatus 110 (see, FIG. 4 below) in a manner, which is transparent to the controlled substance possessor and which requires no input or action on the possessor's part.

As shown in the exemplary method of FIG. 2, the waste containment apparatus 110 is simple to use and requires very little of the controlled substance possessor's time. The relative ease and speed with which a CS waste dose may be deposited and secured within the waste containment apparatus 110 may ensure that the wasting process is completed immediately after administration, or at least in a more timely manner.

Returning to the block diagram of FIG. 1, the waste containment apparatus 110 described herein may generally comprise an input device 130, a collector 140, an (optional) on-board analyzer 150, an information reconciler and recorder 160, a disposer 170 and a transmitter 175. Other components not specifically mentioned herein may also be included within the waste containment apparatus 110 to support or supplement the functionality of the disclosed components. For example, it will be understood that the waste containment apparatus 110 may further comprise a power supply, power converter and/or battery for supplying power to the waste containment apparatus.

The input device 130 may generally comprise one or more input devices for receiving the log-on credentials from the controlled substance possessor, receiving information specific to the CS waste dose (e.g., NDC number, drug type, concentration and original volume of the controlled substance prior to administration) and displaying a confirmation code corresponding to the waste process. Exemplary input devices 130 may include, but are not limited to, a biometric sensor, a barcode scanner, a keypad and a display screen with or without touch screen capabilities. Information received by the input device 130 may be stored within a storage medium of the information reconciler and recorder 160.

The collector 140 may be generally configured for receiving each individual CS waste dose in a single-dose container. According to one embodiment, the collector 140 may be implemented as a carousel comprising a plurality of cuvettes, which are configured for receiving each individual waste dose, as shown in FIGS. 6-9 and FIGS. 10-15 and discussed in more detail below. However, collector 140 may be alternatively implemented in other embodiments. According to one embodiment, the waste dose may be accepted into a new, serialized, barcoded single-dose disposable cuvette. In some cases, the cuvette may be capable of holding up to about 10 ml of waste; however, cuvettes capable of receiving smaller or larger volumes of waste may also be considered. As described in more detail below, the cuvettes are secured within the waste containment apparatus 110, cannot be tampered with, and enable the volume of waste to be measured and the composition and concentration of the waste to be analyzed (if equipped with the optional analyzer).

If included, analyzer 150 may be used to determine the composition and concentration of the CS waste dose deposited into each single-dose container of collector 140. Ideally, analyzer 150 is capable of determining the composition and concentration of the deposited CS waste dose without destroying the deposited substance, so that follow-up testing and verification of a sample is an option if a discrepancy is noted between the measurement/analysis results and the information entered via the input device(s) for the deposited CS waste dose. Multiple techniques are available for the analyzer 150 including, but not limited to, ion mobility spectroscopy, visible or infra-red optical absorption spectroscopy, Raman scattering spectroscopy, fluorescence spectroscopy, gas chromatography, liquid chromatography, gas-liquid chromatography, mass spectrometry, capillary electrophoresis, surface plasmon resonance, optical biosensor array, immunologic based biochemical assays, semiconductor biosensor array, or by any spectrophotometric or spectrometric technique, or by a combination of techniques.

Five principal issues may determine the choice of the analytical technique or combination of techniques that are needed for successful implementation of the analyzer 150:

Many different classes of controlled substances may need to be identified, but at the same time, the analyzer 150 may need to be capable of distinguishing between closely related substances.

The analysis may need to be quantitative and sufficiently accurate to detect dilution of wastage, and to prevent diversion of a fraction of wastage followed by make-up volume replacement with another clear liquid to compensate for the diverted volume.

If the analyzer 150 uses disposable elements to identify and quantify controlled substances, the calibration of the disposable elements may need to be certified and traceable to standards acceptable to regulatory agencies.

The results of the analysis may need to be available within an acceptably short period of time; otherwise, practitioners would be delayed in returning to their clinical duties while awaiting the analytical results.

The analyzer 150 must be sufficiently sensitive to identify and quantify the concentration over a wide dynamic range. To illustrate this point, the narcotic fentanyl (fentanyl citrate) is supplied at a concentration of 0.05 mg/mL (50 parts per million) because of its high potency, and in some circumstances, may be further diluted to only 0.02 mg/mL before administration. In contrast, the narcotic meperidine (meperidine hydrochloride) may be supplied and administered at a concentration of up to 100 mg/mL (100,000 parts per million) since it is of lower potency.

Although many different analysis techniques are available, analyzer 150 may use any analysis technique that produces a precise analysis of the composition and concentration of the CS waste dose deposited within each single-dose container. In some embodiments, analyzer 150 may also measure the volume of the deposited CS waste dose. Alternatively, separate volume measurement means 155 may be provided for determining the amount or volume of the waste dose. In one embodiment, for example, the single-dose containers (e.g., cuvettes 144 of FIG. 6) included within the collector 140 may be the volume measurement means 155, which is configured for detecting a volume of the deposited CS waste dose. In another embodiment, the amount or volume of the deposited CS waste dose may be detected using one or more volume measurement means 155, such as a laser level, a weight measurement, a camera site level reading or a flowmeter.

Figure 7:
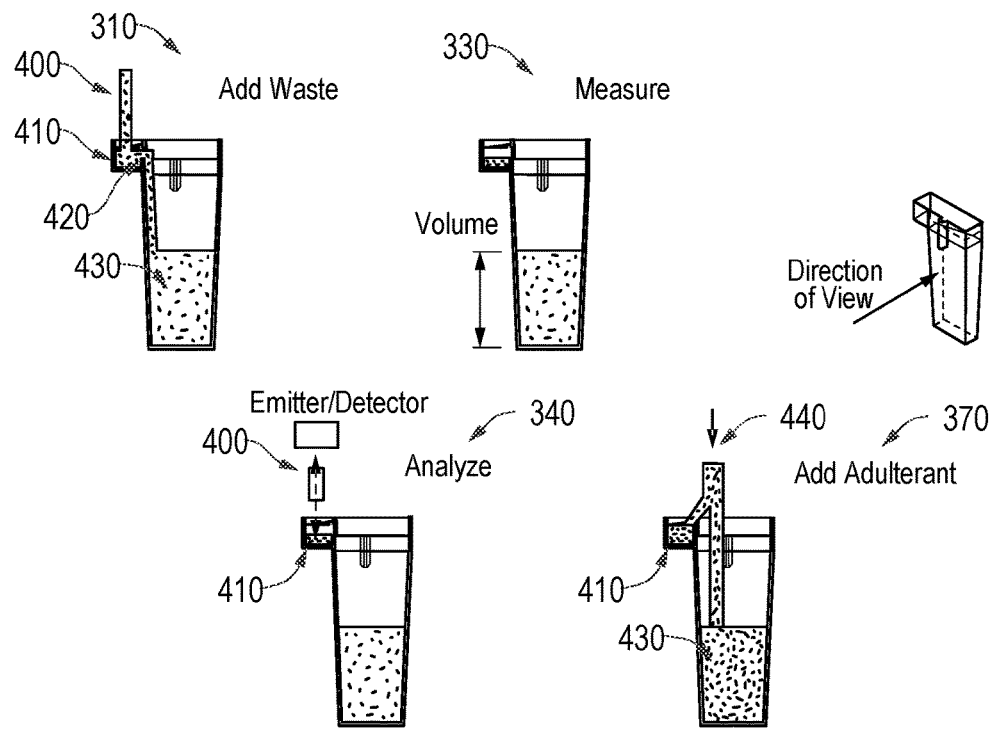
FIG. 7 is a pictorial diagram illustrating certain steps of the method shown in FIG. 4 pertaining to the measurement, analysis and disposal of the controlled substance received within the cuvette, according to one embodiment.

According to one embodiment, analyzer 150 may use a reflectance/absorption technique to analyze and verify the composition and concentration of the deposited CS waste dose, as shown in the pictorial diagram of FIG. 7. In particular, analyzer 150 may use a reflectance/absorption technique configured to capture a spectral signature created through Rayleigh scattering of light as it is reflected off a sample of the deposited CS waste dose. As such, analyzer 150 may include one or more emitters (e.g., one or more light emitting diodes, LEDs) and one of more photodetectors (e.g., one or more photodiodes, such as silicon photodiodes or LEDs configured for detecting light), as shown in FIG. 7. To capture a spectral signature or "fingerprint" of the sample, the emitter(s) transmit light into the sample at different wavelengths and different intensities. The Rayleigh scattered light reflected by the surface of the sample excites the photodetector(s), which provide a measure of the amount of reflected light at each wavelength. The intensity of the reflected light at each wavelength can be used to generate the spectral signature or "fingerprint" of the sample.

Figure 5:
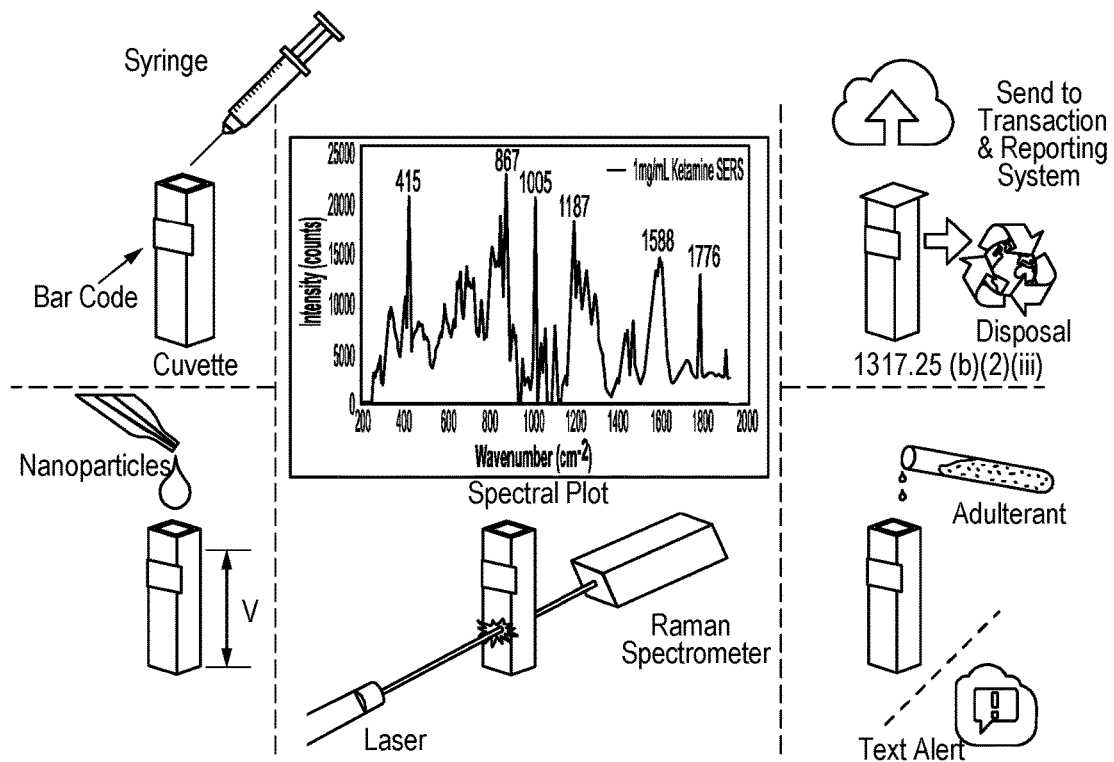
FIG. 5 is a pictorial diagram illustrating one embodiment of the method shown in FIG. 4.
Figure 8:
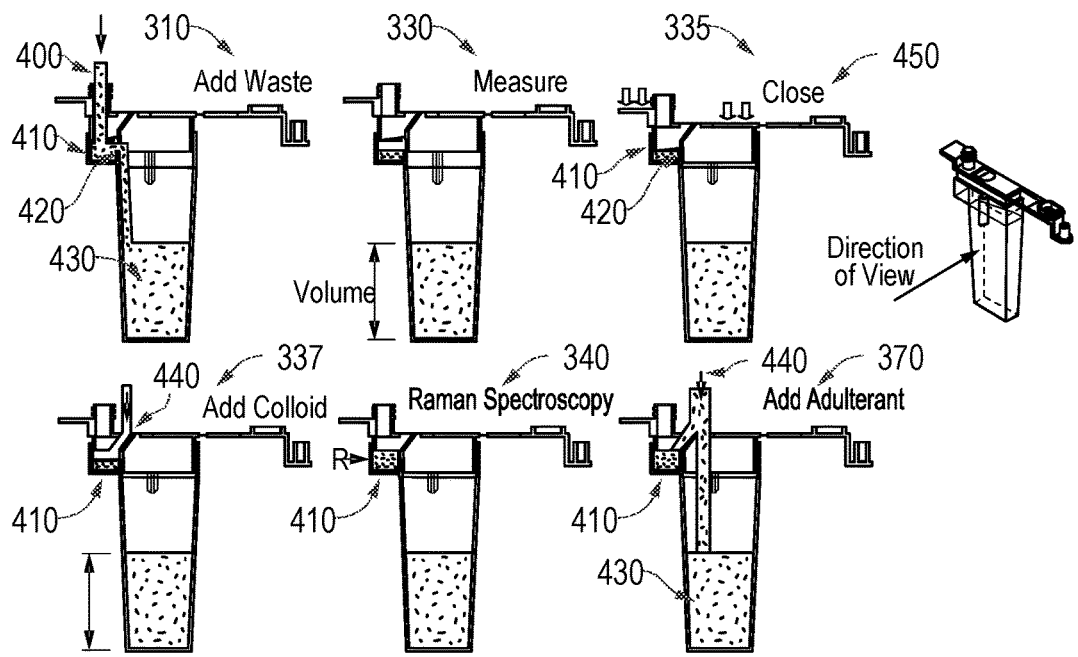
FIG. 8 is a pictorial diagram illustrating certain steps of the method shown in FIG. 4 pertaining to the measurement, analysis and disposal of the controlled substance received within the cuvette, according to another embodiment.

According to another embodiment, analyzer 150 may utilize Raman spectroscopy to analyze and verify the composition and concentration of the deposited CS waste dose, as shown in the pictorial diagrams of FIGS. 5 and 8. Raman spectroscopy is a spectroscopic technique used to observe vibrational, rotational, and other low-frequency modes in a system, and is commonly used to provide a fingerprint by which molecules can be identified. In Raman spectroscopy, a sample is illuminated with monochromatic light, usually from a laser in the visible, near infrared, or near ultraviolet range. The laser light interacts with molecular vibrations, photons or other excitations in the scattering medium, resulting in the energy of the laser photons being shifted up or down. The shift in energy gives information about the vibrational or rotational modes in the scattering medium. Since the modes available for this process depend on the molecular structure of the scattering medium, the Raman spectrum or Raman scatter plot is determined by the scattering material. The Raman scatter plot (see, e.g., FIG. 5) is unique to the chemical structure of a compound and is highly repeatable. The Raman scatter plot may be compared to a gold-standard scatter plot of a specific drug to identify and verify the deposited CS waste dose. However, spontaneous Raman scattering is typically very weak, and as a result, the main difficulty of Raman spectroscopy is separating the weak inelastically scattered light from the intense Rayleigh scattered laser light.

In some embodiments, an advanced type of Raman spectroscopy may be used by analyzer 150, including but not limited to, surface-enhanced Raman, resonance Raman, tip-enhanced Raman, polarized Raman, stimulated Raman (analogous to stimulated emission), transmission Raman, spatially offset Raman, and hyper Raman. In Surface-Enhanced Raman Spectroscopy (SERS), for example, the Raman scatter is enhanced by adding rough metal surfaces or nanoparticles, such as plasmonic-magnetic silica nanotubes, to the deposited CS waste dose. In some cases, the enhancement factor can be as much as $10^{10}$ to $10^{11}$, which means that the SERS technique may be used to detect single molecules.

Once analyzer 150 has determined the composition and/or concentration and/or volume/quantity of a CS waste dose deposited into a single-dose container of the collector 140, the results are stored within the information reconciler and recorder 160, reviewed and reconciled. During the review process, information reconciler and recorder 160 compares the results of the analysis performed by the analyzer 150 and/or the volume measurement results to the information specific to the CS waste dose received via the input device 130.

In an exemplary embodiment, a successful review would indicate that the information about the controlled substance deposited in the single-dose container of the collector 140 is identical to the information provided by the controlled substance possessor via the input device 130. An unsuccessful review would indicate that the information about the controlled substance deposited in the single-dose container of the collector 140 is not identical to information provided by the controlled substance possessor via the input device 130. For example, review might indicate that the deposited substance differed in concentration, composition, and/or volume/quantity from the information provided by the controlled substance possessor. In the event of an unsuccessful review, a discrepancy may be noted and the substance deposited in the single-dose container of the collector 140 may be sequestered in the single-dose container, and may optionally be retested or stored for further review at a later time. In some cases, the record keeping authority 210 may be notified of the discrepancy, e.g., via a text message, instant message, page, email, phone call or other communication technique.

The information reconciler and recorder 160 may generally comprise a storage medium for storing information pertaining to the identity of the controlled substance possessor (e.g., the log-on credentials), information received by the input device 130 about the deposited CS waste dose (e.g., NDC number, drug type, concentration and original volume of the controlled substance prior to administration), information pertaining to the analysis results provided by the analyzer 150 (e.g., composition, concentration and/or volume of the deposited CS waste dose) and/or any other information pertinent to the tracking, verification and drug disposal process. This information (or at least a subset of this information) may be stored within storage medium as a waste transaction record for each deposited CS waste dose. Waste transaction records corresponding to a plurality of CS waste doses may be stored within the storage medium for any length of time, and may persist or be deleted once the waste transaction records are transmitted to the tracking and reporting system 120.

In general, the storage medium included within information reconciler and recorder 160 may comprise any non-transitory computer readable storage medium including, but not limited to, a hard disk drive, a flash memory, a cache, a random-access memory and/or any other storage device or storage disc in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disc, and to exclude propagating signals and transmission media.

In some embodiments, information reconciler and recorder 160 may additionally comprise hardware and/or software for reviewing and/or reconciling the analysis results provided by analyzer 150 and/or the volume measurement results with the information received by the input device 130. Such hardware and/or software may include a processing and/or controller unit, such as but not limited to a central processing unit (CPU), a microprocessor, a microcontroller, an application specific integrated circuit (ASIC), a field programmable gate array (FPGA) or firmware. As used herein, the term "processing unit" is intended to encompass all forms of hardware, firmware or programmable logic that may be used for performing the reviewing and/or reconciling functions of the information reconciler and recorder 160.

In some embodiments, information reconciler and recorder 160 may be configured to execute a set of program instructions (i.e., software) for reviewing and/or reconciling the analysis results and/or the volume measurement results provided by analyzer 150 with the information received by the input device 130. The term "program instructions" may generally refer to commands within a program, which are configured to perform a particular function, such as but not limited to, receiving input signals, recording such input signals, comparing input signals and/or data received from analyzer 150 to the input signals and/or data received from input device 130, recording the comparison results, and sending output signals. The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), or other technologies or methodologies, as desired. In some embodiments, the program instructions may be stored within storage medium 162, or within a read-only memory (ROM) or random-access memory (RAM) residing within information reconciler and recorder 160. Alternatively, the program instructions may be stored within another storage medium external to, yet operably coupled to the information reconciler and recorder 160.

After review and reconciliation are completed, the deposited CS waste dose may be rendered unusable for human consumption by the disposer 170 if there are no noted discrepancies. Rendering the substance "unusable for human consumption" may be accomplished by any suitable chemical, thermal, or mechanical process. Exemplary methods for rendering a controlled substance unusable for human consumption are disclosed in commonly assigned U.S. Pat. No. 9,302,134, which is incorporated herein. According to one embodiment, disposer 170 may add an agent to a CS waste dose deposited into a single-dose container of the collector 140 to oxidize, denature, adulterate, destroy, neutralize and/or disinfect the waste to render it non-infectious and/or unusable for human consumption. According to another embodiment, disposer 170 may add an absorbent material to the CS waste dose deposited into a single-dose container of the collector 140, or to a waste storage bin into which the contents of the single-dose container are dumped to convert the waste into a solid form to render it irretrievable.

If a discrepancy is noted by the information reconciler and recorder 160, the deposited CS waste dose will be secured, sequestered and preserved in its deposited form within the single-dose container of the collector 140. In some embodiments, a message may be sent immediately to a pharmacist, charge nurse or other responsible personnel to notify him/her of the discrepancy, either by text, instant message, page, email, phone call or some other communication means. No indication may be provided to the controlled substance possessor who deposited the CS waste dose.

Figure 10:
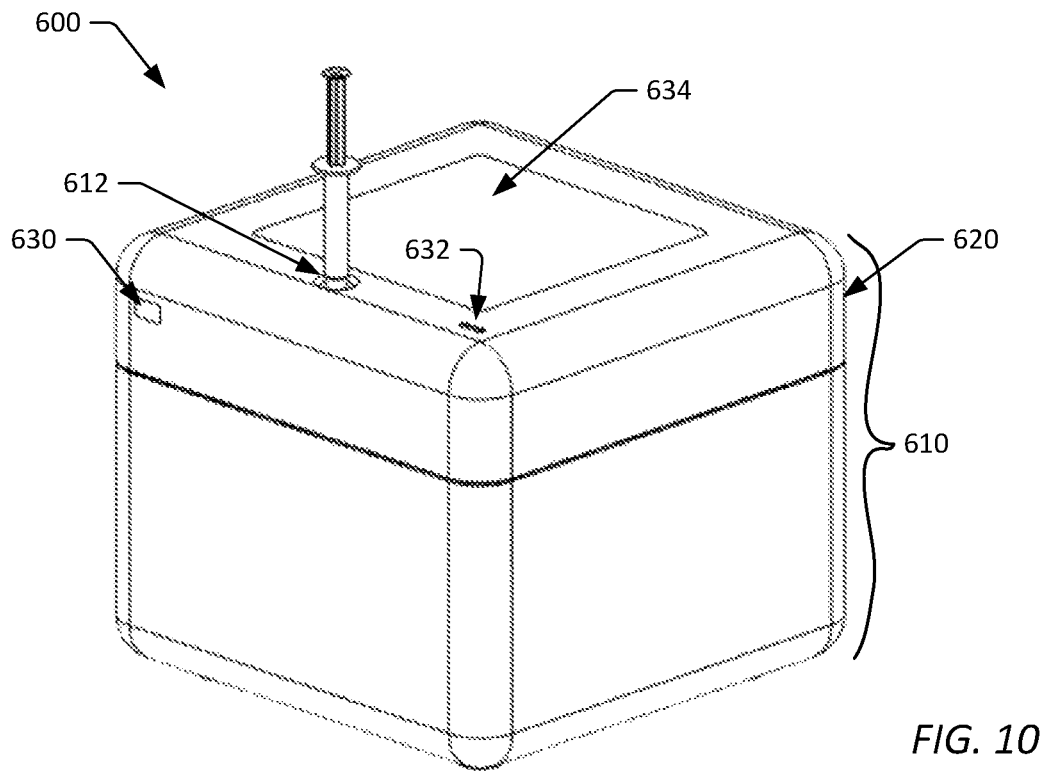
FIG. 10 is a perspective view illustrating another embodiment of a waste containment apparatus comprising a carousel having a plurality of cuvettes placed thereon and secured within the waste containment apparatus.
Figure 11:
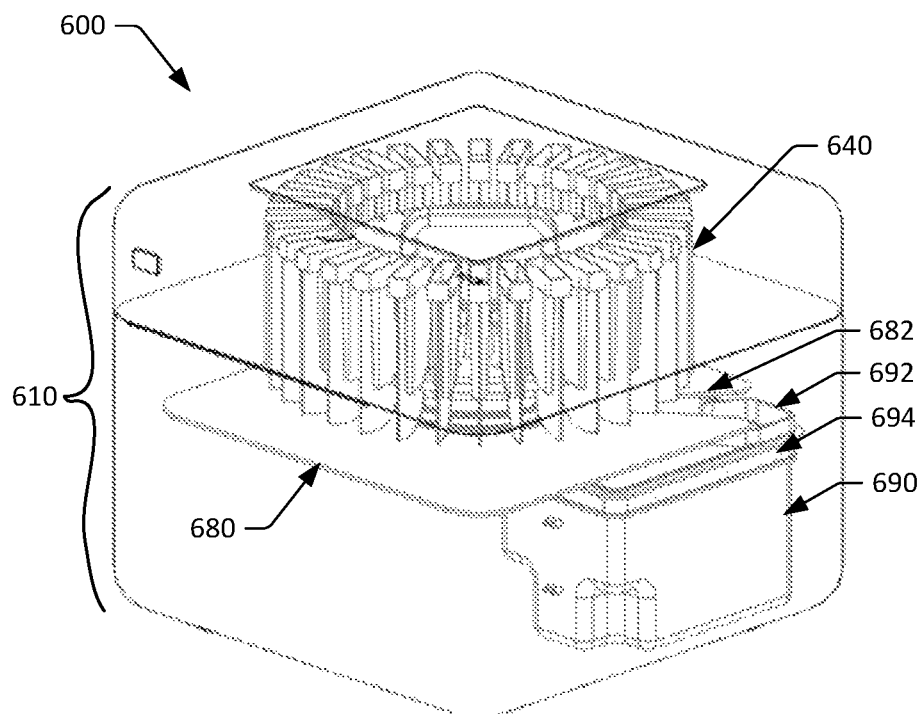
FIG. 11 is a perspective view of the waste containment apparatus shown in FIG. 10 where the housing of waste containment apparatus is rendered transparent to illustrate certain waste collection and disposal components contained therein.

Once the deposited CS waste dose is rendered unusable for human consumption, or sequestered within the collector 140 if a discrepancy is noted, a waste transaction record is compiled, optionally stored within storage medium 162 of the information reconciler and recorder 160 and transmitted to the tracking and reporting system 120. Exemplary embodiments of a waste transaction record are illustrated in FIGS. 10 and 11 and discussed in more detail below.

In some embodiments, tracking and reporting system 120 is operably coupled for receiving and storing the waste transaction records compiled by the information reconciler and recorder 160 of each waste containment apparatus 110. As noted above, "operably coupled" means connected in such a way that data may be exchanged across a communication link 176, such as a wireless network, the Internet, an intranet, or dedicated lines. In some embodiments, tracking and reporting system 120 may be located remote from the waste containment apparatus(es) 110 and may receive the waste transaction records over a wired or wireless communication link 176. In such an embodiment, tracking and reporting system 120 may comprise a remote computer system or server, which is coupled to the waste containment apparatus(es) 110 via a wired or wireless network of substantially any network topology.

According to one particular embodiment, tracking and reporting system 120 may be implemented as a cloud-based computing system. In a cloud-based implementation, apparatus(es) 110 may communicate with tracking and reporting system 120 via a dual redundant wireless connection to ensure reliable operation. In some embodiments, the redundant connection may be powered by a computer system or server, which may also monitor the status of all apparatus(es) 110 included within the controlled substance waste tracking and disposal system 100 to access operational reliability. In some embodiments, software running in the cloud-based tracking and reporting system 120 may also be a part of this reliability monitoring system, for example, by monitoring system availability. Variances in system performance may be reported to personnel, so that replacement of faulty apparatus(es) may be scheduled. However, the tracking and reporting system is not limited to a cloud-based system, and may be alternatively implemented in other embodiments.

In other embodiments (not shown), tracking and reporting system 120 may reside within and/or be distributed across a plurality of network connected waste containment apparatuses 110. In such an embodiment, each waste containment apparatus 110 may store its own waste transaction records, and in some cases, may store a copy of waste transaction records received from other network connected waste containment apparatuses 110. In some cases, the network connected waste containment apparatuses 110 may be connected in a mesh network topology, so that each apparatus 110, or node, relays data throughout the network. However, the network connected waste containment apparatuses 110 are not limited to a mesh network topology, and may be implemented using other network topologies in other embodiments.

In some embodiments, tracking and reporting system 120 may compile and store a comparison database from data collected from all waste containment apparatus(es) 110 connected to the tracking and reporting system 120. In other embodiments, tracking and reporting system 120 may compile and store a comparison database from data collected from only one WCA 110, or more than one WCA but less than all WCAs 110 included within the system 100. In some embodiments, the comparison database may comprise the waste transaction records transmitted from apparatus(es) 110 to the tracking and reporting system 120, and optionally, may also comprise analysis data provided by analyzer 150.

When Raman spectroscopy is used to analyze the composition and concentration of a deposited waste dose, for example, the Raman scatter plot (see, e.g., FIG. 5) generated by the analyzer 150 may also be transmitted to the tracking and reporting system 120 and stored within the comparison database. In some embodiments, tracking and reporting system 120 may compare the Raman scatter plots generated for each specific drug in its database to a gold-standard scatter plot of that drug to verify the deposited CS waste dose. In some embodiments, tracking and reporting system 120 may use the comparison results to update the gold-standard scatter plots stored therein. This may allow the tracking and reporting system 120 to maintain an accurate and up-to-date gold-standard scatter plot for each drug in its database. The most recent gold-standard scatter plot for each drug may be downloaded to all apparatus(es) 110 to maintain drug identification accuracy at a high level.

Figure 4:
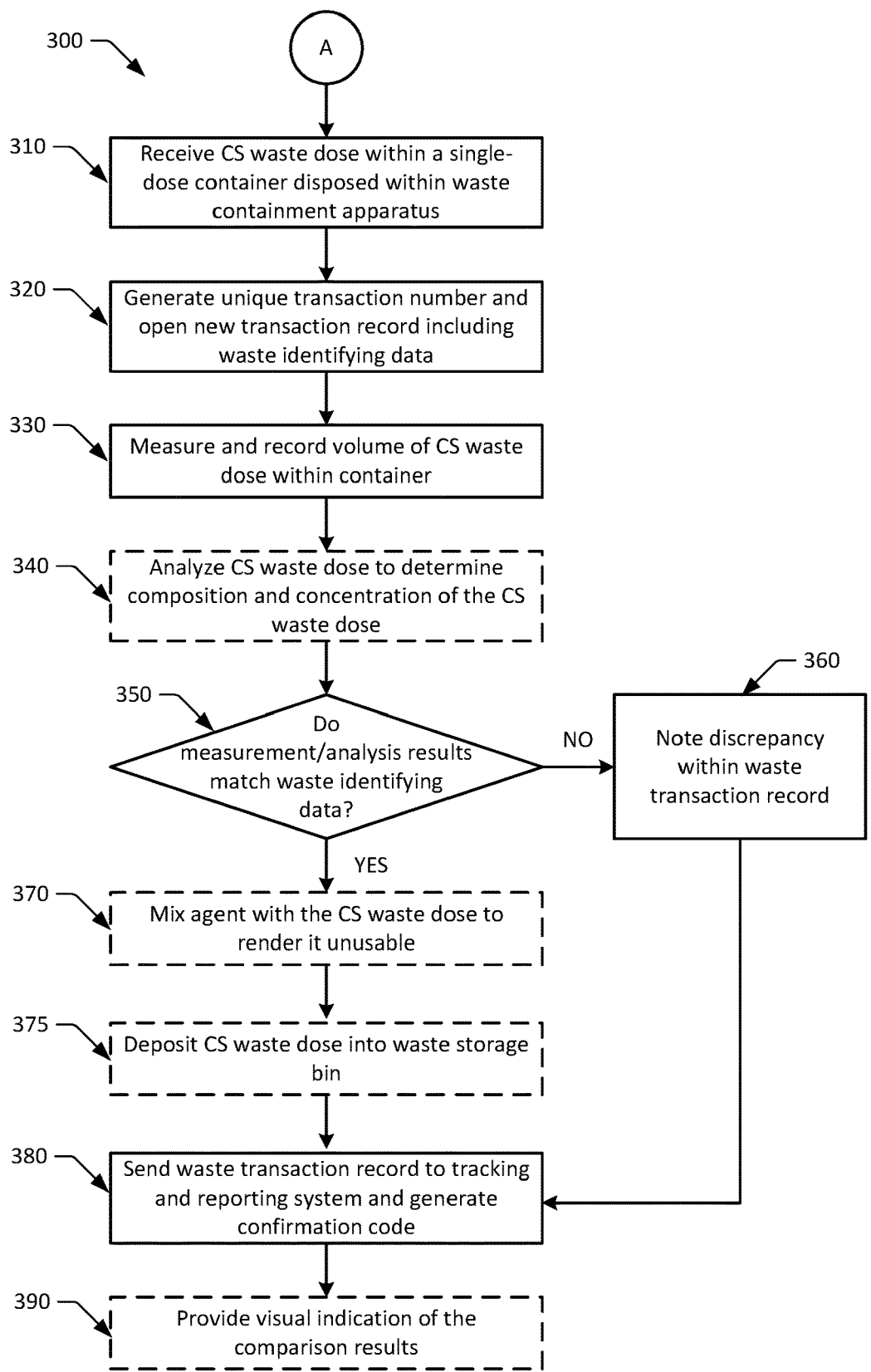
FIG. 4 is a flowchart diagram illustrating an embodiment of a method, which is performed by the waste containment apparatus for analyzing, recording and verifying the controlled substance and reporting results to the tracking and reporting system.

FIG. 4 is a flowchart diagram illustrating one embodiment of a method 300, which may be performed by the waste containment apparatus 110 for analyzing, verifying and adulterating/sequestering a deposited CS waste dose, and for reporting results of such processes (e.g., waste transaction records) to the tracking and reporting system 120. FIG. 5 is a pictorial diagram illustrating certain steps of the method 300 shown in FIG. 4, according to one embodiment.

According to one embodiment, method 300 may begin after a CS waste dose is deposited into the waste containment apparatus 110 in step 280 of FIG. 2 and received within a single-dose container 144 disposed within the waste containment apparatus 110 in step 310 of FIG. 4. According to one embodiment, the single-dose container 144 may be a new, serialized, bar coded single-dose disposable cuvette, as discussed above. Upon receiving the CS waste dose, a unique transaction number is generated and a waste transaction record is opened in step 320. In some embodiments, the unique transaction number may be generated from, or be identical to, the serial number of the single-dose container 144. The data received by the input device 130 about the deposited CS waste dose (e.g., NDC number, drug type, concentration and original volume of the controlled substance prior to administration) is stored within the waste transaction record, along with the log-on credentials of the controlled substance possessor and information pertaining to the waste containment apparatus 110 (e.g., the serial number of the apparatus, the physical location of the apparatus, etc.) obtained in steps 260 and 270 of FIG. 2. In step 330, the volume of the deposited CS waste dose is measured and recorded in the waste transaction record.

In some embodiments, the controlled substance may be analyzed to determine the composition and concentration of the deposited CS waste dose in optional step 340. Although many different analytical techniques may be used in step 340, a colloidal suspension of nanoparticles may be added to at least a portion of the deposited CS waste dose and a Surface-Enhanced Raman Spectroscopy (SERS) technique may be used to determine the composition and concentration of the controlled substance. As shown in the pictorial diagram of FIG. 5, this may be done by illuminating the controlled substance with a focused laser beam and capturing the Raman scatter to produce a Raman spectral plot. The nanoparticles added to the control substance enhance and amplify the Raman scatter to provide exceptional sensitivity. The Raman spectral plot (see, e.g., FIG. 5) is unique to the chemical structure of a compound, is highly repeatable, and may be compared to a gold-standard scatter plot of a specific drug to identify and verify the deposited CS waste dose. The analysis results may be stored within the waste transaction record.

In step 350, the measurement and/or analysis results from steps 330 and 340 are compared with the data received by the input device 130 about the deposited CS waste dose (e.g., NDC number, drug type, concentration and original volume of the controlled substance prior to administration). If the measurement/analysis results do not match the received data (NO branch of step 350), a discrepancy is noted within the waste transaction record in step 360, and the deposited CS waste dose is sequestered in its original form. In step 380, the waste transaction record noting the discrepancy is sent to the tracking and reporting system 120 and a confirmation code is generated. In some embodiments, the waste transaction record may alternatively be stored within the waste containment apparatus 110 for later transmission to the tracking and reporting system 120.

If any discrepancies are noted in step 360, the person tasked with waste compliance (e.g., the record keeping authority 210 of FIG. 1) may be notified by the tracking and reporting system 120, and all pertinent information may be made available so that the person in charge can quickly and efficiently address the discrepancy. In some embodiments, notification may occur immediately after a discrepancy is noted in step 360, for example, by initiating a text message, instant message, email, page or phone call to the record keeping authority 210 or other person tasked with waste compliance. In other embodiments, notification may not occur immediately after a discrepancy is noted in step 360. If a discrepancy is noted in step 360, the controlled substance is sequestered in its original form in the single dose container and tagged, so that it can be handled per the policies and procedures in place at the hospital. These may include re-testing internally or sending out to a lab for testing.

If the measurement/analysis results from steps 330/340 match the received data (YES branch of step 350), the deposited CS waste dose may, in some embodiments, be rendered unusable for human consumption in optional step 370. According to one embodiment, an agent and/or an absorbent material may be added to the deposited CS waste dose to render the controlled substance non-infectious, unusable and/or irretrievable (e.g., converted into a solid form). However, the controlled substance may also be rendered unusable by any other suitable chemical, thermal, or mechanical process, as noted above and described in U.S. Pat. No. 9,302,134.

According to one embodiment, an agent configured to denature, adulterate and/or destroy a controlled substance may be added to a CS waste dose deposited into a single-dose container to render the controlled substance unusable for human consumption. In addition or alternatively, an agent configured to neutralize/disinfect infectious materials may be added to a deposited CS waste dose to render it non-infectious. The term denature, as used herein, refers to changing the chemical composition of a substance (versus inducing a physical change of the substance, such as its state of matter). Examples of denaturation processes include oxidation-reduction reactions and decomposition reactions, but other types of reactions may be considered. The term adulterate, as used herein, refers to debasing or making impure a substance by addition of another substance. The term destroy, as used herein, refers to rendering a substance into a useless form beyond repair or renewal. The term disinfect, as used herein, refers to the destruction of disease-carrying microorganisms. Example disinfecting agents include, but are not limited to, chlorine-releasing chemicals, such as but not limited to sodium dichloroisocyanurate (NaDCC or SDIC). When SDIC is dissolved in water or similar liquids, it hydrolyzes to form hypochlorous acid. As this occurs, high levels of chlorine are liberated which not only serves as a disinfectant but also oxidizes any compound or substance dissolved within the liquid.

According to one embodiment, once the controlled substance is rendered unusable for human consumption by the addition of an agent in optional step 370 of FIG. 4, the unusable substance may remain within the single-dose container 144 until the single-dose containers are retrieved for storage and/or disposal. In one example, the record keeping authority 210 (or other person tasked with waste compliance) may periodically collect the single-dose containers 144 contained within the waste containment apparatus(es) 110. In some cases, the record keeping authority 210 may store collect the single-dose containers 144 within a locked bin for later pickup and incineration by a reverse distributor, as described in more detail below with respect to FIGS. 16 and 20. Alternatively, the record keeping authority 210 (or other person tasked with waste compliance) may dispose of the single-dose containers 144 within the trash after contents within the single-dose containers have been verified, documented and rendered unusable for human consumption.

According to another embodiment, once the CS waste dose is rendered unusable for human consumption by the addition of an agent into the single dose container 144 in optional step 370 of FIG. 4, the unusable substance may be deposited into a waste storage bin in step 375. One example of a waste storage bin is shown in FIG. 11 and described in more detail below. According to yet another embodiment, the CS waste dose may be deposited into the waste storage bin in step 375 after its contents are verified in step 350, yet before an agent is added to the single dose container 144 to denature, adulterate, destroy, neutralize and/or disinfect the controlled substance. In other words, optional step 370 may be omitted and the original contents deposited into the single-dose container 144 may be deposited into the waste storage bin in step 375, once verification of the contents is complete.

In either embodiment, an absorbent material may be added to the contents contained within the waste storage bin to render such contents unusable, irretrievable and/or in a form suitable for non-regulated waste disposal. In some cases, an absorbent material may be introduced into the waste storage bin after each CS waste dose is deposited therein, or after multiple CS waste doses from a plurality of single-dose containers 144 have been deposited into the waste storage bin. In other cases, an absorbent material may be added to the waste storage bin at any time prior to, or during, removal of the waste storage bin from the waste containment apparatus 110. Examples of absorbent materials that may be added to the contents contained of the waste storage bin to render such contents unusable, irretrievable and/or in a form suitable for non-regulated waste disposal are disclosed, for example, in U.S. Pat. No. 9,302,134. Other absorbent materials not specifically mentioned therein may also be considered, as long as such materials render the waste storage bin contents unusable, irretrievable and/or in a form suitable for non-regulated waste disposal.

In one example, a super absorbent polymer (SAP) may be added to the waste storage bin to convert the contents contained therein into a solid or semi-solid form. In another example, a SAP combined or mixed with an agent, which is configured to denature, adulterate, destroy, neutralize and/or disinfect a controlled substance (such as NaDCC or SDIC) may be added to the waste storage bin. Mixtures of SDIC and SAP are available commercially and can be acquired inexpensively. Some examples include, Liqui-Loc Plus™ and Isolyser®-LTS-Plus™. Liqui-Loc Plus™ is EPA approved and registered (EPA Registration Number 87708-1-37549), and suitable for approved solid waste landfills and incineration. It is noted that the absorbent materials and agents described herein need not be limited to the noted examples of SAPs or SDIC. Rather, such citations have been provided as example compounds and agents which may be used in the systems, apparatuses, and methods described herein.

Figure 16:
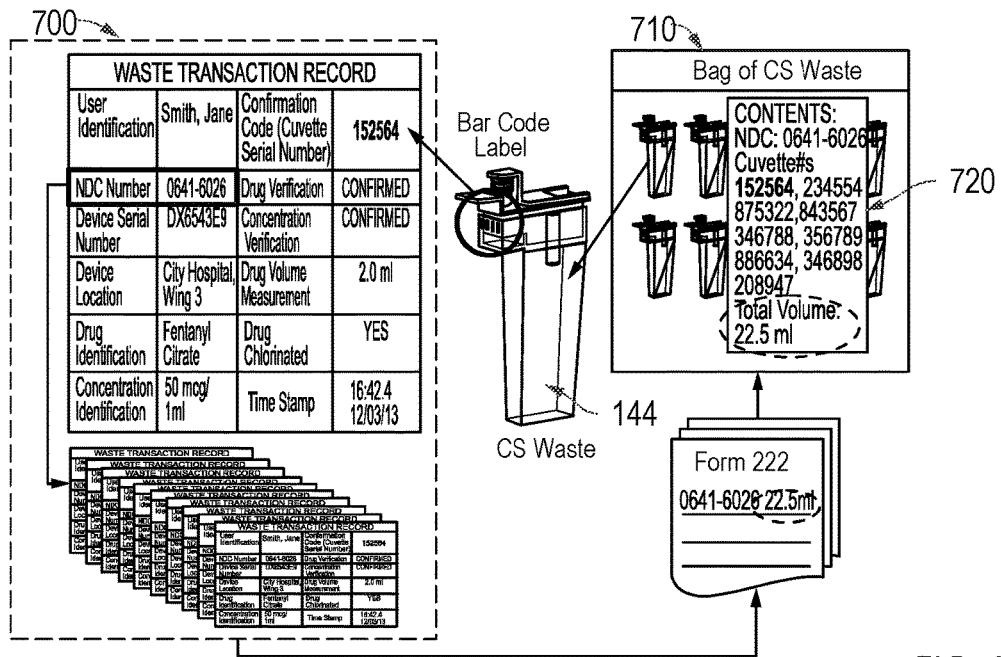
FIG. 16 is a pictorial diagram illustrating one embodiment of a waste transaction record produced by a waste containment apparatus.
Figure 17:
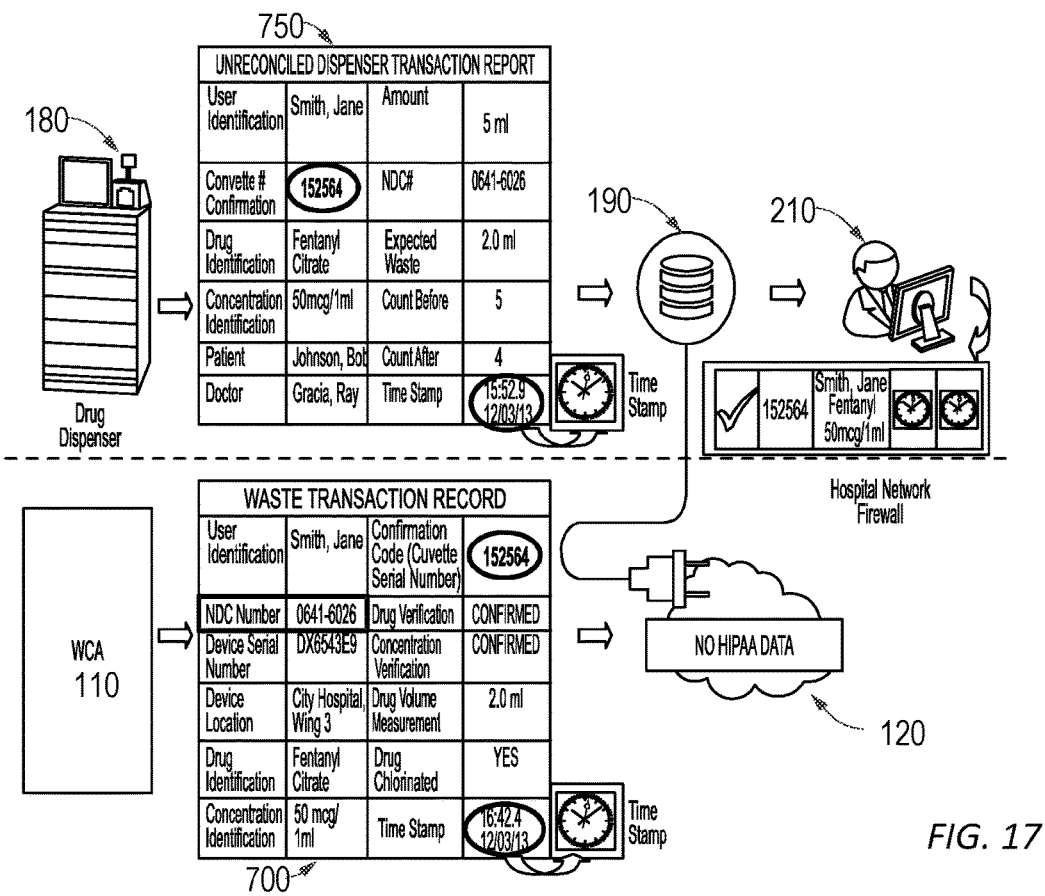
FIG. 17 is a pictorial diagram illustrating one embodiment of the reconciliation performed by a record keeping authority between the waste transaction records generated by the waste containment apparatus and corresponding hospital records.

In step 380 of FIG. 4, the waste transaction record is sent to the tracking and reporting system 120 and a confirmation code is generated and provided to the controlled substance possessor. In some embodiments, the waste transaction record may be optionally stored within the waste containment apparatus 110, for example, within storage medium 162 of information reconciler and recorder 160. Exemplary embodiments of a completed waste transaction record are illustrated in FIGS. 16 and 17. As described in more detail below with respect to FIG. 19, the confirmation code generated in step 380 of FIG. 4 may be entered into ADM 180 by the controlled substance possessor (in step 1000 of FIG. 19), so as to correlate the waste transaction record with a corresponding dispenser transaction report. In some embodiments, the confirmation code may comprise, or may be equivalent to, the unique transaction number generated in step 320 of FIG. 4. In one particular example, the confirmation code may comprise, or may be equivalent to, the serial number of the single-dose container 144 containing the deposited CS waste dose, as shown in FIGS. 16 and 17 and discussed in more detail below.

In step 390, visual indication of the comparison results obtained in step 350 are provided on the collector. Although depicted as occurring after the waste transaction record is sent to the tracking and reporting system 120 in step 380, visual indication of the comparison results may be provided any time after the comparison is performed in step 350. Although depicted as an optional step (with dashed lines), providing visual indication of the comparison results enables the status of the single-dose containers 144 (e.g., confirmed drug match, unconfirmed drug match, or unused) to be quickly and efficiently determined by the record keeping authority. Visual indication of the comparison results is generally not provided to the depositor of the controlled substance waste dose. As discussed in more detail below with reference to FIG. 9, visual indication of the comparison results may be provided on the collector via light emitting devices (e.g., LEDs), which are arranged on the collector adjacent to the single-dose containers 144 for displaying the status of the comparison results determined for each single-dose container. Alternative implementations utilizing other light emitting devices or other forms of visual indication may also be considered.

Figure 6:
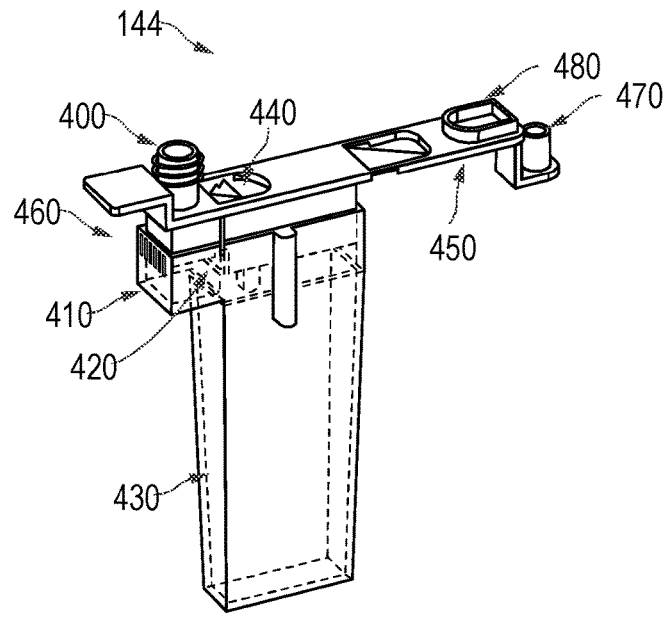
FIG. 6 is a perspective view illustrating one embodiment of a cuvette configured for receiving a controlled substance.

FIG. 6 is a perspective view illustrating one embodiment of a cuvette 144, which may be configured for receiving a single CS waste dose and for reserving at least a portion of the deposited waste for analysis by various analytical techniques including, but not limited to, reflectance/absorption and Raman spectroscopic techniques. As shown in the exemplary embodiment of FIG. 6, cuvette 144 may comprise a first inlet port 400 for receiving the CS waste dose and an analysis chamber 410 for reserving a fixed amount of the received waste for analysis. A spillway with gate valve 420 arranged on a sidewall near the top of the analysis chamber 410 ensures that the fixed amount of waste remains in the analysis chamber 410 even as more waste enters the cuvette via inlet port 400 and spills over into storage chamber 430.

According to one embodiment, analysis chamber 410 may be configured for reserving about 0.5 ml of waste, and storage chamber 430 may be configured for storing up to about 10 ml of waste. Such volumes may be appropriate for analyzing and storing a typical post-patient controlled substance waste dose. However, analysis chamber 410 and storage chamber 430 are not restricted to any particular volume of waste, and may be alternatively configured for reserving and storing substantially less than, or substantially more than, the exemplary volumes mentioned above.

In one example, analysis chamber 410 may be configured for reserving about 0.1 ml to about 2 ml of waste, and storage chamber 430 may be configured for storing about 5 ml of waste to about 20 ml of waste when cuvette 144 is used for receiving a post-patient controlled substance waste dose. However, cuvette 144 is not restricted to receiving a post-patient controlled substance waste dose, and may alternatively be used for receiving other controlled substances (e.g., other pharmacological or non-drug controlled substances). If used for receiving other controlled substances, analysis chamber 410 and/or storage chamber 430 may be configured for reserving and/or storing substantially less than, or substantially more than, the exemplary volume ranges noted above, depending on the controlled substance(s) they are intended to receive.

According to one embodiment, analysis chamber 410 and/or storage chamber 430 may be formed from an optically transmissive material to facilitate waste analysis within analysis chamber 410 and/or volumetric measurements within storage chamber 430. Alternatively, analysis chamber 410 and/or storage chamber 430 may be formed from an optically opaque material if optical transparency is not required for the analysis or measurement procedures.

As shown in FIG. 6, cuvette 144 may comprise a second inlet port 440 for introducing nanoparticles and/or an agent into the analysis and storage chambers 410 and 430. As shown in FIGS. 7-8, the second inlet port 440 may comprise a first branch and a second branch to separately communicate the nanoparticles and/or an agent into the analysis chamber 410 and the storage chamber 430. According to one embodiment, cuvette 144 may comprise a flip-top sealing cap 450 that may be articulated to seal off the analysis chamber 410 from the storage chamber 430. Sealing off the analysis chamber 410 may be required for certain analytical techniques, but not for others. In some embodiments, sealing cap 450 may be closed to facilitate certain analytical techniques, such as the Raman spectroscopy technique discussed in FIG. 8 below.

In other embodiments, sealing cap 450 may be closed to seal analysis chamber 410 and storage chamber 430, such that contents contained therein are temporarily secured (e.g., for transport) or permanently inaccessible and irretrievable. As shown in FIG. 6, for example, protruding portions 470 and 480 of the sealing cap 450 may be configured to securely engage with the first inlet port 400 and the second inlet port 440, respectively. By secure engagement, it is meant that the protruding portions 470 and 480 comprise a size and shape that provide a tight fit when protruding portions 470 and 480 are inserted into first inlet port 400 and second inlet port 440. This tight fit may prevent the contents contained within cuvette 144 from spilling when cuvette 144 is transported. In some embodiments, secure engagement may be additionally provided by a latch or other locking mechanism, which may be located on the protruding portions 470 and 480 and/or on the first and/or second inlet ports 400 and 440 for locking the sealing cap 450 in place and rendering the contents within cuvette 144 permanently inaccessible and irretrievable. In such embodiments, sealing cap 450 may provide an additional or alternative safe guard, which prevents the contents of cuvette 144 from being accessed or retrieved.

Although not limited to this particular design, the cuvette 144 shown in FIG. 6 is advantageously designed to receive and sequester each individual CS waste dose, and provides a dual-chamber design that reserves a portion of the deposited controlled substance waste for analysis (by various analytical techniques), while providing sufficient storage for the remaining waste. The cuvette 144 also meets all DEA requirements for an "inner liner," and allows tracking and identification with a unique barcode label 460 comprising, e.g., a cuvette serial number. As another advantage, the analysis chamber 410 and/or storage chamber 430 may be formed from an optically transmissive material to facilitate volumetric measurements and/or waste analysis. This enables highly accurate and repeatable analysis and measurement techniques to be used to verify the contents of the deposited CS waste dose.

FIGS. 7-8 are pictorial diagrams illustrating various steps of the method 300 shown in FIG. 4 pertaining to the measurement, analysis and (optional) adulteration of a CS waste dose. The pictorial diagrams shown in FIG. 7 illustrate a portion of the method steps shown in method 300, according to one embodiment, in which a reflectance/absorption technique (e.g., a Rayleigh scattering technique) is used to analyze the controlled substance in step 340 of FIG. 3. In the pictorial diagrams shown in FIG. 8, a Raman spectroscopy technique is used in analysis step 340. Corresponding method steps are depicted with like numerals in FIGS. 4, 7 and 8.

As depicted in FIGS. 7 and 8, a CS waste dose is received within a cuvette 144 in step 310 through the first inlet port 400. In step 310, a fixed amount of the received waste dose remains within analysis chamber 410, while the remainder of the waste dose spills over spillway 420 into storage chamber 430. In step 330, a volume of the waste within the storage chamber 430 is measured, e.g., via a machine vision measurement of waste volume. As noted above, the volumetric measurement may be recorded within the waste transaction record pertaining to that particular cuvette.

In the embodiment shown in FIG. 7, the fixed amount of the received waste dose remaining within the analysis chamber 410 may be analyzed using a reflectance/absorption (e.g., Rayleigh scattering) technique in step 340. In one example, an emitter and detector may be arranged above the first inlet port 400 for illuminating the waste dose sample within the analysis chamber 410 with light and for detecting a portion of the light, which is reflected back to the detector. In FIG. 7, however, sealing cap 450 is not present during the analysis step 340, thus providing the emitter and detector with a clear line of sight into the analysis chamber 410. In some cases, the emitter may be configured for emitting one or more wavelengths of light, wherein selection of such wavelengths is dependent on the drug being analyzed. The emitter may also be configured for emitting light at different intensities for each of the one or more wavelengths. The use of different intensities allows more resolution in the wavelengths transmitted by the emitter. In some cases, the detector may be a broad spectrum photodetector configured for detecting a wide range of wavelengths. As noted above, the composition and concentration of the waste dose may be determined by capturing the spectral signature created through Rayleigh scattering of light as it is reflected off the dose sample within the analysis chamber 410.

According to one embodiment, emitter and detector may be part of a device, which generates a spectral signature created through Rayleigh scattering of light as it is reflected off a sample, and captures a "fingerprint" unique to each drug being identified. This low cost technique depends on a multi-spectral illumination of the sample, which differs from the more traditional method of using white light and then splitting the reflected light into various spectral components using a diffraction grating. In the device used herein, multiple spectral frequencies are analyzed via the use of multiple LED emitters, each illuminating at a different spectral value. Broadband photodetectors are included to detect the amount of light reflected from the sample at each emitted wavelength. This technique reduces the complexity, and therefore the cost, of drug identification and allows for a much smaller footprint and reduced power requirement for the analyzer 150. In some embodiments, drug fingerprints may be stored within the waste containment apparatus 110 and/or the tracking and reporting system 120, and compared to new samples taken for drug identification. In some embodiments, drug fingerprints may be averaged over time to maintain an accurate comparison database within the waste containment apparatus 110 and/or the tracking and reporting system 120.

In the embodiment shown in FIG. 8, the fixed amount of the received waste dose remaining within the analysis chamber 410 may be analyzed using a Raman spectroscopy technique. Raman spectroscopy requires additives to be mixed with the waste sample in specific proportions. Prior to conducting the analysis step, the flip-top sealing cap 450 may be placed on the cuvette in step 335 of FIG. 8 to close off the spillway 420 and ensure that a fixed amount of waste remains in the analysis chamber 410. By positioning the sealing cap 450 onto the cuvette, a gate valve on the underside of the cap 450 closes off the spillway 420 to provide a closed volume within the analysis chamber 410 containing a known amount of waste. In step 337, a colloidal suspension of nanoparticles (and optionally salt) can be added to the analysis chamber 410 via the second inlet port 440 to condition the waste sample for Raman spectroscopy. In step 340, the waste sample within the analysis chamber 410 may be illuminated with a focused laser beam and the Raman scatter may be captured to produce a Raman spectral plot (see, e.g., FIG. 5), which is unique to the chemical structure of the waste sample. The Raman spectral plot may then be compared to a gold-standard scatter plot of a specific drug to identify and verify the deposited CS waste dose.

Once analysis is complete and the analysis results are compared with the received data in step 350 of FIG. 4, an agent configured to denature, adulterate, destroy, neutralize and/or disinfect a controlled substance may optionally be added in step 370 via the second inlet port 440 to the controlled substance contained within the analysis chamber 410 and the storage chamber 430 to render the controlled substance unusable for human consumption. As shown in FIGS. 7 and 8, the second inlet port 440 may comprise a first branch and a second branch to separately communicate the agent into the analysis chamber 410 and the storage chamber 430 to render the controlled substance contained therein non-infectious and/or unusable for human consumption.

Figure 9:
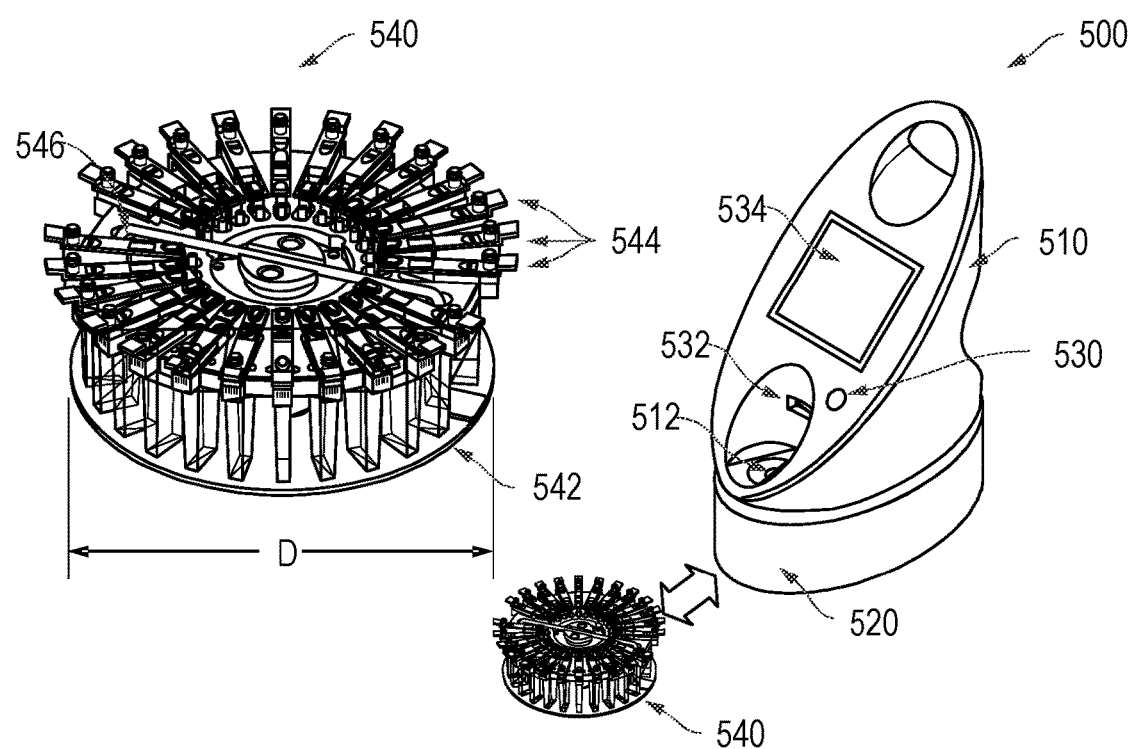
FIG. 9 is a perspective view illustrating one embodiment of a waste containment apparatus comprising a carousel having a plurality of cuvettes placed thereon and secured within the waste containment apparatus.

FIG. 9 is a perspective view illustrating one embodiment of a waste containment apparatus 500 and a collector configured for holding a plurality of cuvettes for secure containment within the waste containment apparatus. More specifically, waste containment apparatus 500 illustrates one embodiment of a physical implementation of the waste containment apparatus 110 shown in block diagram form in FIG. 1. Waste containment apparatus 500 includes many of the same components shown in FIG. 1 and described above, such as input device 130, collector 140, analyzer 150, information reconciler and recorder 160, disposer 170 and transmitter 175. Many of these components are disposed within, or configured to be disposed within housing 510 of the waste containment apparatus 500, and thus, are not shown in FIG. 9. Description of the components disposed within housing 510 is not repeated for purposes of brevity. It is noted that, although housing 510 is illustrated in FIG. 9 as having a particular form factor, the waste containment apparatus 110 shown in block diagram form in FIG. 1 is not limited to such a housing, and may be alternatively implemented in other embodiments. FIGS. 10-11 illustrate an alternative implementation of a waste containment apparatus.

As shown in FIG. 9, waste containment apparatus 500 may include a waste input port 512 configured for receiving a CS waste dose, a slide-out drawer 520 configured for housing a collector 540, and one or more input devices (e.g., biometric sensor 530 and barcode scanner 532) configured for receiving information about the controlled substance possessor and/or information about the CS waste dose to be deposited into the collector 540 via the waste input port 512. In some embodiments, waste containment apparatus 500 may include a display screen 534 for displaying a confirmation code once a deposited CS waste dose has at least been sequestered within a cuvette. In some cases, display screen 534 may also be used for entering information pertaining to the controlled substance possessor and/or the CS waste dose to be deposited into the collector 540.

In general, waste input port 512 may be configured for receiving a CS waste dose in one or more forms. In some embodiments, waste input port 512 may be configured for receiving a liquid CS waste dose, e.g., from a syringe or vial. In other embodiments, waste input port 512 may be configured for receiving a solid CS waste dose, e.g., in the form of a pill or patch. The size and shape of the waste input port 512 may vary, depending on the form of the CS waste dose the input port is configured to receive. When configured for receiving pills or patches, e.g., waste input port 512 may comprise a circular or elliptical opening or an elongated slit, which is large enough to receive a range of sizes of pills and patches. When configured for receiving a liquid CS waste dose, on the other hand, waste input port 512 may comprise a relatively small opening configured for receiving a hypodermic needle, or a slightly larger opening through which the liquid dose can be poured.

In the embodiment shown in FIG. 9, collector 540 is implemented as a carousel 542 having the plurality of cuvettes 544 placed thereon and arranged in a ring. The carousel 542 may be generally dimensioned to fit within the slide-out drawer 520 of the waste containment apparatus 500. In one embodiment, a diameter (D) of the carousel 542 may range between about 6 inches and about 18 inches. Although collector 540 is depicted as a carousel 542 having a plurality of cuvettes 544 placed thereon and arranged in a ring, collector 540 is not so limited and may be alternatively implemented in other embodiments.

As shown in the exemplary embodiment of FIG. 9, the waste containment apparatus 500 may comprise a convenient removable carousel 542 to simplify the workflow associated with transporting the cuvettes 544 to/from the pharmacy. In one example, carousel 542 may serve as a tote to hold the cuvettes 544 in the pharmacy, in transit to the waste containment apparatus 500, and inside the apparatus 500 itself. In some embodiments, carousel 542 may include a retractable handle 546 to aid in carrying the carousel.

According to one exemplary embodiment, carousel 542 may be loaded in the pharmacy with new disposable cuvettes 544 and taken by a pharmacy technician to a waste containment apparatus 500. The slide-out drawer 520 may have a locking mechanism, which the technician may open with a key, barcode scan or fingerprint scan, for example. Once authorized access is granted, the technician may remove the existing carousel containing used (and potentially unused) cuvettes 544 from the apparatus 500, and replace the existing carousel with a carousel containing new, unused cuvettes. The carousel 542 may be placed into, and removed from, the waste containment apparatus 500 as a single unit to make refilling quick and easy. Once the drawer 520 on the waste containment apparatus 500 is closed, the apparatus may automatically account for the new cuvettes and resume operation.

In some embodiments, the pharmacy technician (or another record keeping authority 210) may periodically collect the used/unused cuvettes 544 from the waste containment apparatus 500, place them in a locked bin in the pharmacy, and/or stage for pickup by a reverse distributor as required by the facility's policies and procedures. Due to the design of carousel 542, the cuvettes 544 may be transported back to the pharmacy as a single unit. In some embodiments, the cuvettes 544 may be set aside (e.g., in a locked bin in the pharmacy) until someone is ready to empty and sort the used cuvettes. In some embodiments, carousel 542 may incorporate its own logic and/or processing unit to remember which cuvettes were used, which were not, and which had a discrepancy of some sort.

According to one embodiment, carousel 542 may provide visual indication of the comparison results (generated in step 350 of FIG. 4) by illuminating each cuvette 544 with a color of light (e.g., red, green, or yellow) specific to the comparison results to allow for quick and efficient sorting by the pharmacist. In one example, visual indication of the comparison results may be provided by a plurality of light emitting devices (such as light emitting diodes, or LEDs) and associated on-board illumination system on the carousel 542. In general, one or more LEDs may be arranged adjacent to a different one of the cuvettes 544 for providing a visual indication of the comparison results for each individual cuvette.

In some cases, a single LED package, containing multiple LEDs, capable of emitting light over a wide range of visible wavelengths may be arranged adjacent to each cuvette 544 for providing a visual indication of the comparison results. In such cases, the single LED package may be configured for generating different colors of light (e.g., red, yellow and green) by modifying the amplitude and/or pulse frequency of the drive current supplied to the LED. In other cases, multiple LEDs may be arranged adjacent to each cuvette 544 for providing a visual indication of the comparison results. In such cases, each of the multiple LEDs may be configured for generating a different color of light.

According to one embodiment, the on-board illumination system may comprise driver circuitry for supplying the plurality of LEDs/single LED package with a drive current sufficient to produce a particular color of light (e.g., red, yellow or green), a processor for receiving and processing the status of each cuvette 544, and non-volatile memory for storing the current status of each cuvette 544. In some embodiments, the on-board processor of carousel 542 may be powered by a battery, and in some cases, a rechargeable battery. If a rechargeable battery is included, the battery may be periodically recharged, in one example, via built-in wireless magnetic charging hardware included within the carousel 542. Other means for recharging a rechargeable battery may also be used.

According to one embodiment, carousel 542 may further comprise a wireless communication system, which may receive status information from a control unit within waste containment apparatus 500 for updating the status of cuvettes 544. Carousel 542 may retain the received status information within the attached non-volatile memory when the carousel is removed from the waste containment apparatus 500 and transferred to the pharmacy.

In some embodiments, the status of each cuvette 544 may be illuminated when a button on the carousel 542 is momentarily pressed. After the carousel 542 is reloaded with empty cuvettes, the same button (or a different button on carousel 542) may be pressed for a particular duration of time (e.g., more than 3 seconds) to reset all status indicators (e.g., LEDs) to the empty status color, and to reset the cuvette status stored within the non-volatile memory.

In other embodiments, the status of each cuvette 544 may be illuminated after the comparison step 350 of FIG. 4 is completed, and may remain illuminated until a cuvette 544 is removed from the carousel 542 and/or replaced with an empty cuvette. In such embodiments, removal of a cuvette 544 and/or replacement with an empty cuvette may cause the status indicators (e.g., LEDs) to be reset to the empty status color and the cuvette status stored within the non-volatile memory to be reset.

According to one embodiment, all cuvettes 544 with a confirmed match and adulterated CS waste dose may be illuminated with red light. All red-illuminated cuvettes may be placed in a locked bin for the reverse distributor to account for when they come to collect the used cuvettes for incineration at a later date. No bar code scanning or review of these cuvettes is necessary. All waste transaction records for these cuvettes were created by the waste containment apparatus and sent to the tracking and reporting system 120. This greatly reduces the load on the pharmacy.

According to one embodiment, all cuvettes 544 with an unconfirmed drug match and non-adulterated CS waste dose may be illuminated with yellow light. The yellow-illuminated cuvettes, of which there should be relatively few, indicate that the substance inside the cuvette is not what it is supposed to be. This could indicate diversion, such as substitution of the drug with saline, or there could be another explanation. To keep all options open for the pharmacist, any drug which cannot be confirmed by the waste containment apparatus will be sequestered and preserved; no adulteration is ever performed on the yellow-illuminated cuvettes. This provides the pharmacist with the option of sending the drug out for laboratory testing.

In a simplified apparatus where the optional on-board analyzer 150 has been omitted, the yellow-illuminated cuvettes may alternatively identify waste from individuals whom the Director of Pharmacy has designated for waste audit. This may be done by flagging the individual's user profile in the tracking and reporting system 120 from the pharmacist's console (described below with respect to FIG. 11). In this case, any waste deposited into the waste containment apparatus by these individuals will be flagged for easy segregation. This waste can be tested offline under the direction of the Director of Pharmacy. This eliminates the need for the pharmacy staff to scan cuvettes upon return to the pharmacy and streamlines the workflow.

According to one embodiment, all unused cuvettes 544 may be illuminated with green light. The green-illuminated cuvettes may be left in the carousel 542 and the empty slots may be refilled with new cuvettes. The carousel 542 is now ready for use again. In some embodiments, two or more carousels 542 may be provided for each waste containment apparatus. This may allow the pharmacy greater flexibility, since at any given time there may be a carousel operating inside the waste containment apparatus and one in the pharmacy, either awaiting emptying/refilling, or on the shelf ready to go back into the apparatus.

FIGS. 10-14 illustrate another embodiment of a waste containment apparatus 600 including a collector 540, which is configured for holding a plurality of cuvettes 544 for secure containment within the waste containment apparatus. FIG. 10 provides a front perspective view of waste containment apparatus 600. Like the embodiment shown in FIG. 9, waste containment apparatus 600 includes many of the same components shown in FIG. 1 and described above, such as input device 130, collector 140, analyzer 150, information reconciler and recorder 160, disposer 170 and transmitter 175. Although many of these components, such as analyzer 150, information reconciler and recorder 160, disposer 170 and transmitter 175, are included within the waste containment apparatus 600, they are not illustrated or further described herein for purposes of brevity. In FIG. 11, housing 610 of waste containment apparatus 600 is rendered transparent to illustrate an exemplary arrangement of the waste collection and disposal components contained therein. These components are illustrated and discussed in more detail with respect to FIGS. 12-14.

As shown in FIG. 10, waste containment apparatus 600 includes a waste input port 612 for receiving a CS waste dose, and one or more input devices, such as biometric sensor 630 and barcode scanner 632, for receiving information about the controlled substance possessor and/or information about the CS waste dose to be deposited into the collector 640. Although depicted in FIG. 10 as receiving an injectable liquid, waste input port 612 may be configured for receiving CS waste doses in liquid and/or solid forms. Display screen 634 is included for displaying a confirmation code and/or for entering information pertaining to the controlled substance possessor and/or the CS waste dose to be deposited into the collector 640 of the waste containment apparatus, as described above.

As shown in FIGS. 10-11, the waste collection and disposal components of apparatus 600 may be accessed by opening or removing an upper portion 620 of housing 610. As noted above, a locking mechanism may be provided on housing 610 to prevent unauthorized access to the components disposed therein. In some cases, a pharmacy technician, record keeping authority or other authorized personnel may open the locking mechanism, for example, with a key, barcode scan or fingerprint scan, to gain access to the waste collection and disposal components contained therein.

Figure 13:
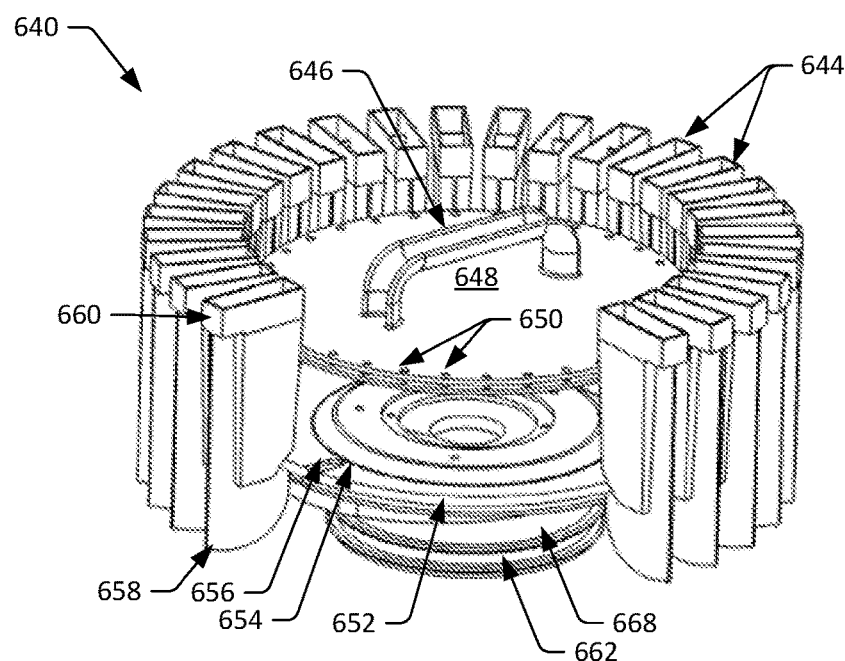
FIG. 13 is a side perspective view of the collector shown in FIG. 12.
Figure 14:
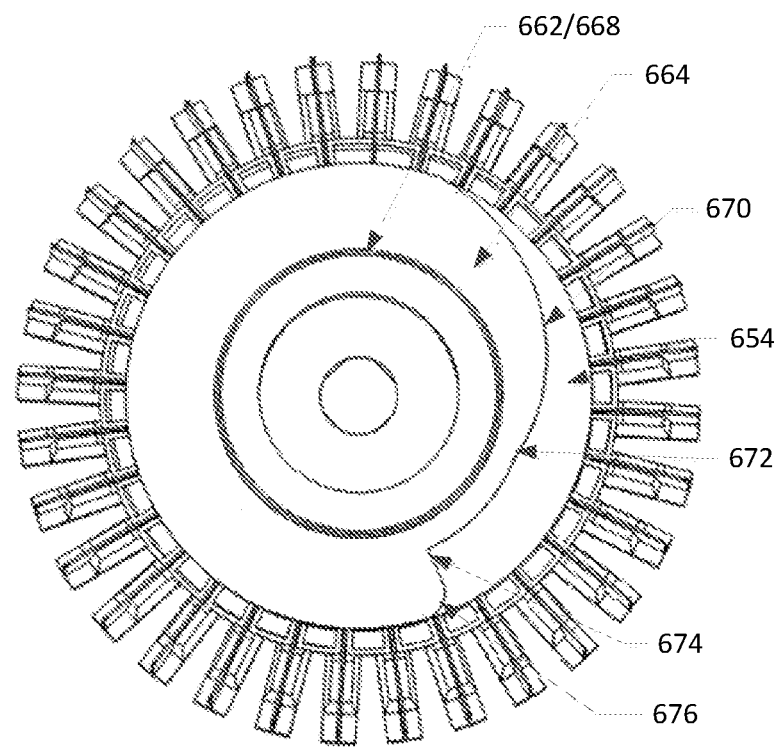
FIG. 14 is a bottom view of the collector shown in FIG. 12.
Figure 15:
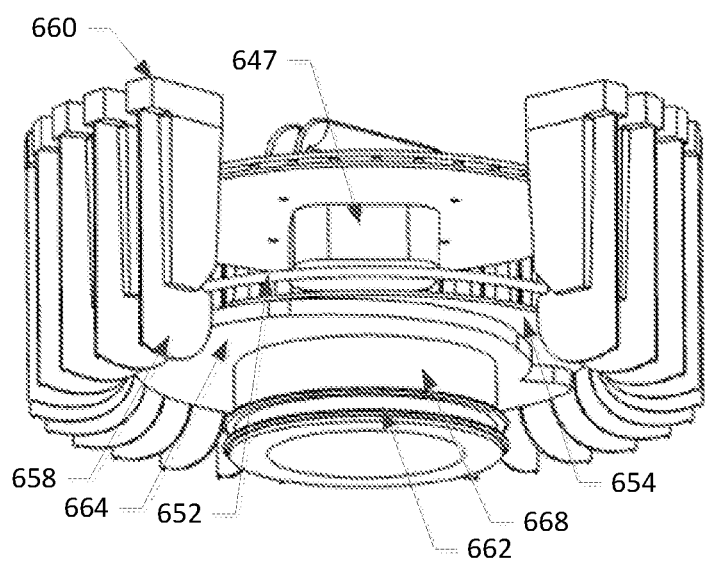
FIG. 15 is another side perspective view of the collector shown in FIG. 12.

As shown in FIGS. 11-15, collector 640 is implemented as a carousel 642 having a plurality of cuvettes 644 positioned thereon and arranged in a ring. As in the previous embodiment, carousel 642 may be generally dimensioned to fit within housing 610, and may have a diameter (D) ranging, in some embodiments, between about 6 inches and about 18 inches. Carousel 642 may also include many of the features described above for carousel 542, such as a handle 646 to aid in carrying the carousel to/from the pharmacy, and visual indicators (e.g., LEDs) to provide visual indication of the cuvette status. In some embodiments, carousel 642 may include an on-board illumination system for driving the visual indicators to display a status of each cuvette 644, a processor for receiving and processing the status of each cuvette 544, and a non-volatile memory for storing the current status of each cuvette 644, as noted above. In some embodiments, a wireless communication system may be included for receiving status information from a control unit within waste containment apparatus 600, which may be used to update the cuvette status stored within the non-volatile memory. In some embodiments, a battery may be included for powering electronic components of carousel 642. In some embodiments, carousel 642 may include an electronics housing 647 for housing electronic components of the carousel, such as but not limited to, the on-board illumination system, processor, non-volatile memory, wireless communication system and battery mentioned above. An exemplary location for the electronics housing 647 is shown in FIG. 15.

Figure 12:
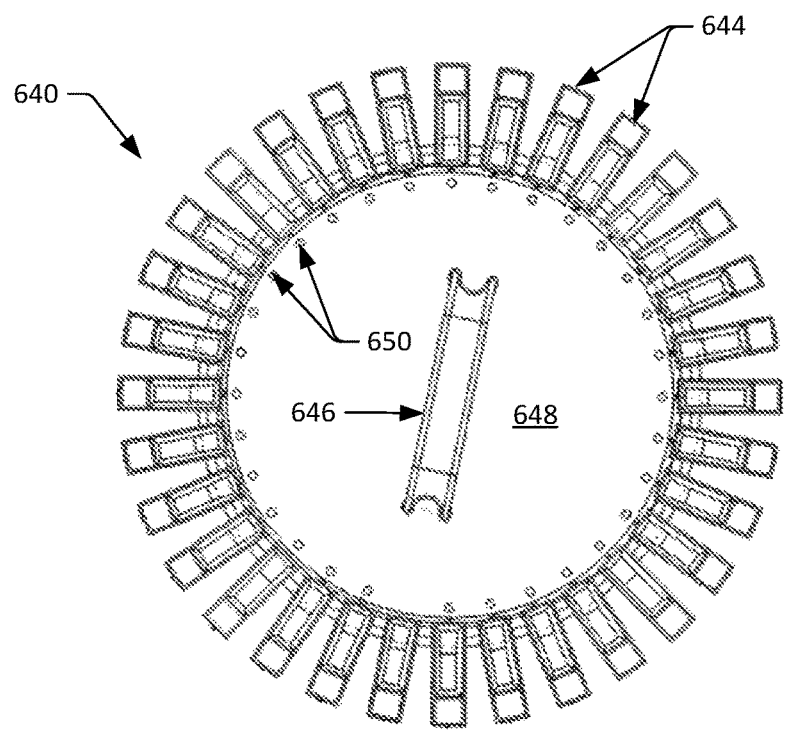
FIG. 12 is a top view of the collector included within the waste containment apparatus shown in FIGS. 10 and 11.

FIGS. 12-13 respectively illustrate a top view and a side perspective view of carousel 642 comprising a plurality of cuvettes 644 positioned thereon and arranged in a ring. As shown in FIGS. 12-13, a handle 646 is positioned on a top plate 648 of the carousel 642 to aid in carrying the carousel, and a plurality of LEDs 650 are arranged near a periphery of the top plate 648, each LED positioned near a corresponding one of the cuvettes 644 for displaying a cuvette status.

As noted above, the plurality of LEDs 650 may each be illuminated with a specific color of light representing the cuvette status for a corresponding cuvette 644. According to one embodiment, the plurality of LEDs 650 may provide a visual indication of the comparison results generated in step 350 of FIG. 4 by illuminating each cuvette 644 with a color of light specific to the comparison results to allow for quick and efficient sorting by the pharmacist. In one such example, all cuvettes 644 with a confirmed match may be illuminated with red light, all cuvettes 644 with an unconfirmed match may be illuminated with yellow light, and all unused cuvettes 544 may be illuminated with green light. According to another embodiment, the plurality of LEDs 650 may provide a visual indication of cuvette use and/or waste auditing. In one such example, red-illuminated cuvettes may identify used cuvettes, green-illuminated cuvettes may identify unused cuvettes, and yellow-illuminated cuvettes may identify waste from individuals whom the Director of Pharmacy has designated for waste audit.

As noted above with regard to FIG. 4, a CS waste dose deposited into a cuvette may be rendered non-infectious, unusable and/or irretrievable (e.g., converted into a solid form) if the measurement/analysis results from steps 330/340 of FIG. 4 match the information received from the controlled substance possessor about the deposited CS waste dose. As noted above, an agent and/or an absorbent material may be added to a deposited CS waste dose to render the controlled substance non-infectious, unusable and/or irretrievable. In some embodiments, an agent may be added to a cuvette 644 to denature, adulterate, destroy, neutralize and/or disinfect the controlled substance contained therein. In other embodiments, the original contents deposited into the cuvette 644 may be deposited into a waste storage bin, once verification of the contents is complete. In some embodiments, an absorbent material may be added to the contents contained within the waste storage bin to render such contents unusable, irretrievable and/or in a form suitable for non-regulated waste disposal. Examples of suitable agents and absorbent materials are discussed above, but are not limited to only those examples mentioned above.

FIG. 11 illustrates one embodiment of a waste storage bin 690, which may be configured for receiving and storing one or more CS waste doses, which are deposited into the waste storage bin from one or more of the cuvettes 644. In some embodiments, waste storage bin 690 may be similar to the receptacles disclosed in commonly assigned U.S. Pat. No. 9,302,134. For example, waste storage bin 690 may include a stored supply of absorbent material, which may be released into the interior of the waste storage bin to render the contents contained therein unusable, irretrievable and/or in a form suitable for non-regulated waste disposal. In some cases, an absorbent material may be introduced into the waste storage bin after each CS waste dose is deposited therein, or after multiple CS waste doses from a plurality of cuvettes 644 have been deposited into the waste storage bin. In other cases, an absorbent material may be added to the waste storage bin at any time prior to, or during, removal of the waste storage bin from the waste containment apparatus 600. Examples of absorbent materials that may be added to the contents contained of the waste storage bin to render such contents unusable, irretrievable and/or in a form suitable for non-regulated waste disposal are disclosed, for example, in U.S. Pat. No. 9,302,134. Other absorbent materials not specifically mentioned therein may also be considered, as long as such materials render the waste storage bin contents unusable, irretrievable and/or in a form suitable for non-regulated waste disposal.

As shown in FIG. 11, carousel 642 is mounted onto a slotted plate 680, which is positioned between the carousel and the waste storage bin 690. The slot 682 formed within the slotted plate 680 is positioned above an opening 692, which is provided on an upper surface 694 of the waste storage bin 690 for receiving CS waste doses from cuvettes 644. According to one embodiment, carousel 642 is further provided with means, which enable a cuvette 644 centered above the slot 682 to pivot away from the top plate 648 of the carousel for the purpose of depositing its contents into opening 692 of the waste storage bin 690. Such means are illustrated more clearly in FIGS. 12-15.

FIGS. 14-15 respectively illustrate a bottom view and another side perspective view of carousel 642 comprising a bottom plate 654 including a slot 656 formed in a periphery of the bottom plate, a ring 652 surrounding the periphery of the bottom plate, and a rotating cam 664 positioned beneath bottom plate. As described in more detail below, the plurality of cuvettes 644 are positioned around a periphery of the top plate 648 and pivotably mounted to the ring 652. It is noted that although top plate 648 and bottom plate 654 are illustrated as being substantially circular in shape, alternative shapes may be considered in other embodiments.

As shown in FIGS. 13-15, bottom plate 654 is centered upon and coupled to a first annular support post 662, while rotating cam 664 is centered upon and coupled to a second annular support post 668. The first annular support post 662 is concentrically arranged within the second annular support post 668. The second annular post 668 is configured to rotate about a central axis extending there through, which enables the rotating cam 664 to rotate independently bottom plate 654. Although not depicted in the figures, a drive mechanism may be coupled to the second annular support post 668 to provide rotational motion of rotating cam 664.

In some embodiments, ring 652 may be coupled to a center post (not shown), which extends along the central axis through support posts 662/668 to couple to top plate 648. The center post may be coupled to the drive mechanism mentioned above (or a separate drive mechanism) to enable top plate 648, ring 652 and/or the plurality of cuvettes pivotably mounted thereon to rotate independently of the bottom plate 654 and/or the rotating cam 664. In such embodiments, the center post may be rotated to position a particular cuvette 644 in alignment for receiving a CS waste dose and/or in alignment for depositing a received CS waste dose into the waste storage bin.

In order to deposit the contents of a particular cuvette 644 into the waste storage bin 690, bottom plate 654 is rotated to align the particular cuvette within the slot 656 formed in the bottom plate 654. Once the cuvette is aligned within slot 656, rotation of the cam 664 causes a lower portion 658 of the cuvette to traverse a contoured surface 670 of the rotating cam 664. All cuvettes not aligned within the slot 656 are in contact with bottom plate 654, and thus, are prevented from traversing the contoured surface 670 of the rotating cam 664. As shown in most clearly FIG. 14, contoured surface 670 gradually decreases the radius of the cam until a minimum radius is reached at wall 674, after which the radius of the cam abruptly increases to a maximum radius. In some embodiments, a peripheral corner 676 of wall 674 may be provided with a rounded edge to assist the lower portion 658 of the cuvette in surmounting the abrupt transition from the minimum radius to the maximum radius, as shown in FIG. 14. The lower portion 658 of the cuvette may also be provided with a rounded edge to assist in the traversal of the contoured surface 270, and to further assist in surmounting the abrupt transition from the minimum radius to the maximum radius.

As shown in FIGS. 14-15, the lower portion 658 of the cuvette may follow the contoured surface 670 of the rotating cam 664 until it encounters a first indentation 672 in the contoured surface. At this point, the upper portion 660 of the cuvette 644 has pivoted far enough away from the top plate 648 to enable the cuvette contents to pour out of the upper portion 660, through the slot 682 formed in slotted plate 680, and into the opening 692 in waste storage bin 690. The cuvette may remain in this fully pivoted position until cam 664 encounters wall 674. When this occurs, cam 664 rotates in the opposite direction to pivot the cuvette back to its initial position against top plate 648. The rounded surface of the lower portion 658 of the cuvette assists in pivoting the cuvette back to its initial position.

As shown in FIGS. 13-15, carousel 642 uses a camfollower mechanism to pivot the cuvettes 644 away from/toward the top plate 648 of the carousel. In the illustrated embodiment, the "cam" is provided by the rotating cam 664, while the "follower" is provided by the lower portion 658 of each cuvette. In such an embodiment, rotation of the cam is translated into linear motion of the follower by pivotably mounting the cuvettes 644 onto ring 652, and providing the cam 664 with a unique contoured surface 670, which a lower portion 658 of a cuvette may traverse to dispense the cuvette contents into the waste storage bin 690. Although a particular cam-follower mechanism is described herein and shown in the figures, carousel 642 is not limited to such a camfollower mechanism and may be alternatively equipped with other means for dispensing the cuvette contents into the waste storage bin.

FIG. 16 is a pictorial diagram illustrating one embodiment of the waste transaction records 600 that may be produced by a waste containment apparatus 110 and sent to the tracking and reporting system 120. In the pictorial diagram of FIG. 16, it is assumed that the CS waste dose deposited within the cuvette 144 remains within the cuvette, as discussed above with regard to FIGS. 7-9. Once removed from the waste containment apparatus 110, cuvettes containing CS waste doses may be stored within a locked bin in the pharmacy until picked up by a reverse distributor.

As noted above with regard to FIG. 4, the waste containment apparatus 110 will generate a separate waste transaction record 700 for each cuvette 144 containing a deposited CS waste dose or waste designated for waste audit. In the exemplary embodiment shown in FIG. 16, waste transaction record 700 includes a user identification (e.g., a name or identification number of the controlled substance possessor), an NDC number, a serial number and physical location of the waste containment apparatus (Device Serial Number and Device Location), a drug identification (e.g., the name of the controlled substance deposited within the cuvette), a drug volume measurement and (optionally) a concentration of the drug. In addition, the waste transaction record 700 may include data indicating whether or not the composition and concentration of the waste sample was verified or confirmed in the optional analysis step, and whether or not the waste dose was adulterated (e.g., chlorinated) or otherwise rendered unusable for human consumption. Furthermore, each waste transaction record 700 may be identified by a confirmation code (e.g., a cuvette serial number read from the bar code label 460 included on the cuvette 144) and may optionally include a time/date stamp indicating exactly when the waste transaction record was created.

As noted above, a reverse distributor may periodically retrieve the used cuvettes from a locked bin in the pharmacy, scan each individual bar code on the cuvettes, group them according to NDC number and place each group within a different bag of waste 710. In some embodiments, the reverse distributor may be given access to the tracking and reporting system 120 to simplify their documentation and chain of custody verification. As shown in FIG. 16, for example, tracking and reporting system 120 may be used to automatically create a single line entry on Form 222 for each group of cuvettes indicated with a specific NDC number (e.g., 0641-6026) and may tally the cumulative volume (e.g., 22.5 mL). This may be repeated automatically for each NDC number, and labels 720 may be printed out to clearly identify the bags of waste 710 for each specific NDC number. As shown in FIG. 16, labels 720 may identify the bag contents by specifying the NDC number, the serial numbers of the cuvettes included within the bag and the total volume of the waste contained therein. After collecting, grouping and documenting the chain of custody verification for all used cuvettes, the reverse distributor may take the cuvettes for disposal in accordance with waste disposal regulations.

In other embodiments, a reverse distributor may not be needed to collect, group, document and dispose of the used cuvettes. In the waste storage apparatus 600 shown in FIGS. 10-11, for example, the cuvette contents are deposited within waste storage bin 690 where the contents may be rendered non-infectious, unusable, and irretrievable by addition of an agent and/or absorbent material into an interior of the waste storage bin. In some cases, such agents and/or absorbent materials may also convert the waste storage bin contents into a form, which is suitable for non-regulated waste disposal. In such cases, the waste storage bin may be disposed in the trash and the reverse distributor may be omitted from the waste disposal process.

FIG. 17 is a pictorial diagram illustrating how a record keeping authority 210 (e.g., a pharmacist) may reconcile the waste transaction records 600 generated by waste containment apparatus 110 and transmitted to the tracking and reporting system 120 with corresponding hospital records stored within the OAIS 190. As noted above, hospital records stored within the OAIS 190 may include, for example, a patient's Medication Administration Report (MAR), a pharmacy report of medications, an anesthesia record, records from ADM 180, and other types of data. In the embodiment shown in FIG. 17, a waste transaction record 700 for a particular controlled substance waste dose is reconciled against a dispenser transaction report 750, which was generated by the ADM 180 that dispensed the controlled substance.

Like the waste transaction record 700, the dispenser transaction report 750 may include a user identification (e.g., a name or identification number of the controlled substance possessor), an NDC number, a drug identification (e.g., the name of the controlled substance deposited within the cuvette), and an original volume (i.e., amount) and concentration of the dispensed drug. In addition, each dispenser transaction report 750 may be identified by a confirmation code (e.g., a cuvette serial number read from the bar code label 460 included on the cuvette 144), a time/date stamp indicating when the dispenser transaction report 750 was created, a patient name and a doctor name. In some embodiments, the dispenser transaction report 750 may also include an expected volume of waste and an inventory count of the controlled substance before and after the controlled substance was dispensed.

According to one embodiment, a reconciliation application may be provided for reconciling waste transaction records 700 with corresponding dispenser transaction reports 750 and/or other hospital records stored within the OAIS 190. The reconciliation application may be run under the control of the record keeping authority 210 (e.g., pharmacist) as an independent application, and may pull in waste transaction records 700 from the tracking and reporting system 120 and dispenser transaction reports 750 from the OAIS 190. Since the dispenser transaction reports 750 can be presented in an industry-standard format (such as .csv or other formats), the reconciliation application will accept these reports 750 and search for matching waste transaction records 700 in the tracking and reporting system 120. Matching records 700/750 will be automatically compared to determine if the expected waste volume matches the actual measured waste volume, and if the NDC numbers match.

Any non-matching records will be tabulated and presented to the record keeping authority 210 as possible discrepancies in a discrepancy report. Since the dispenser transaction reports 750 contain patient specific information (e.g., patient name), it is important that only the record keeping authority 210 running the reconciliation application will have access to the dispenser transaction reports 750; the waste containment apparatuses 110 will not, nor will any information from these reports 750 end up in the tracking and reporting system 120. As shown in FIG. 17, information flow from the waste containment apparatuses 110, to the tracking and reporting system 120, to the reconciliation application run by the record keeping authority 210 is one-way only, and never in the other direction. This ensures that proper HIPAA protections are maintained at all times.

According to one embodiment, the reconciliation application may search for waste transaction records 700 corresponding to the dispenser transaction reports 750 by using the confirmation code stored within 700/750 as a unique identifier. As noted above and described in more detail below, the conformation code may be a unique cuvette serial number, which may be entered as a comment in the ADM transaction record and will not guide or affect the chain of custody in any way. There will be no direct information exchange between the ADM 180 and the waste containment apparatus 110.

The waste transaction records 700 created by the waste containment apparatus 110 can be manually and/or automatically reconciled with the hospital records. The accuracy of the waste containment apparatus 110 can be determined during the reconciliation process, as well as the accuracy of the personnel involved in entering data into the apparatus. In some cases, waste disposal events can be periodically audited by the pharmacy staff against the hospital transaction records and the waste transaction records 700 to assess the performance of the waste containment apparatus 110.

The confirmation code created by the waste containment apparatus 110 at the time of wasting may be the primary matching link between the waste transaction records and the hospital records.

However, since the confirmation code is manually entered (in step 1000 of FIG. 19 below), it can be prone to human error/fraud. Because of this, timestamp analysis may also be used for records reconciliation. Timestamp analysis is error-free, but assumes a sequential relationship between ADM dispensing and waste transactions. It is suggested that the hospital processes reflect regulatory intent and require clinicians to waste a particular dose before acquiring medication for a new patient. This helps ensure a sequential relationship between medication acquisition and medication waste events. Using both confirmation code and timestamp analysis will provide a high degree of certainty, regardless of human error or non-sequential wasting, in reconciling ADM dispensing and waste transactions without requiring integration between the ADM 180 and waste containment apparatus 110.

One goal of the disclosure provided herein is to provide the medical care industry with integrated systems, apparatuses and methods for monitoring drug wastage that are efficient, eliminates the opportunity for redirection and theft, and completes the documentation process required by the DEA as outlined in the Controlled Substances Act of 1970 and the pending new rules. A comparison between the current drug wastage procedure (FIG. 18) and a proposed drug wastage procedure (FIG. 19) shows that the proposed procedure provides a more reliable and accurate alternative to the present norm in which a human witness is required to verify the wastage process.

Figure 18:
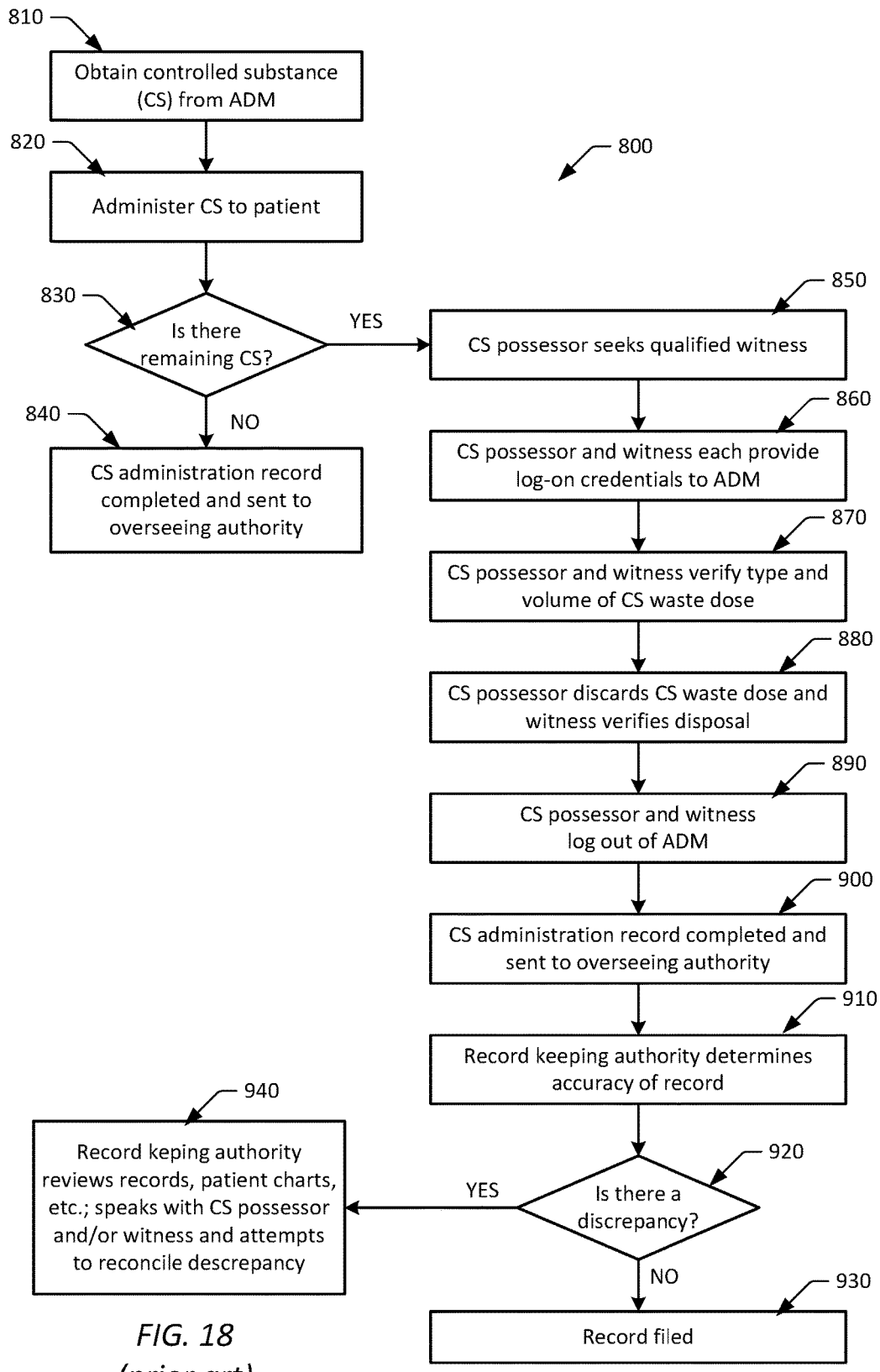
FIG. 18 is a flowchart diagram illustrating a prior art waste procedure at a typical healthcare facility.

The flowchart in FIG. 18 illustrates the current drug wastage procedure 800 for the disposal of controlled substances. The current drug wasting procedure 800 shown in FIG. 18 is typical of many organizations. In step 810, a controlled substance is obtained from a controlled substance source, such as a pharmacy or ADM 180. At many facilities, the Pyxis® or Omnicell® ADM system is utilized. In many cases, the controlled substance is dispensed in a "one-size-fits-all" amount, and is obtained by a clinician or registered nurse upon entering a secure password into the ADM 180.

In step 820, the controlled substance possessor administers the controlled substance according to a prescription, physician order, or laboratory protocol. In step 830, the possessor determines whether or not there is excess controlled substance (i.e., a CS waste dose). If there is no excess of controlled substance (NO branch of step 830), the possessor completes the required controlled substance administration record and returns the record to the pharmacy or overseeing authority 190. If there is an excess of controlled substance (YES branch of step 830), the possessor must dispose the excess substance and therefore seeks a qualified witness in step 850.

In order to properly document the wasting procedure, the possessor and the witness must both go to the ADM 180 and separately provide log-on credentials to the ADM in step 860. The possessor logs-on with his/her credentials and locates the dispenser transaction report 750 associated with the current waste transaction. Screen prompts are followed with instructions for the waste process. During the process, the witness logs-on with their credentials and both the possessor and the witness verify the drug type and volume against the open record in step 870. As mentioned above, all injectable medications are currently clear, so the possibility exists for the possessor to substitute any clear liquid, such as saline or water, and the witness may not be able to notice a difference.

In step 880, the possessor discards the CS waste dose while the witness observes the disposal. In the current drug wastage procedure 800, the CS waste dose is typically disposed of, or wasted, by injection into a sink, expelled onto the floor, or dropped into a needle disposal container. In the case of partially used vials of controlled substances, these are sometimes deposited intact into needle disposal containers and could potentially be retrieved for unauthorized or illicit use. The current disposal methods also present a compliance dilemma in states, such as California, where Schedule II waste is required to be collected for incineration. Once the CS waste dose has been discarded in full view of the witness, the witness verifies the disposal by signature. The signature may be a handwritten signature or an electronic signature or password.

After the witness verifies the disposal, the possessor and witness log out of the ADM in step 890, and the completed controlled substance administration record is completed and carried or sent via computer to the OAIS 190 in step 900. Again, handwritten entries on the administration form contribute to errors that must be corrected.

In step 910, the record keeping authority 210 determines the accuracy of the controlled substance administration record. If there is no discrepancy in step 920, the record is filed in step 930. If there is a discrepancy, the record keeping authority 210 reviews records, patient charts, etc., and speaks with the possessor and witness in an attempt to reconcile the discrepancy in step 940. Unfortunately, the record keeping authority 210 frequently does not have an opportunity to review and reconcile the records immediately. Additionally, the records may have errors due to handwriting, the possessor completing several disposals at the same time, and the time elapsed between the administration of the controlled substance and the disposal of any excess.

Figure 19:
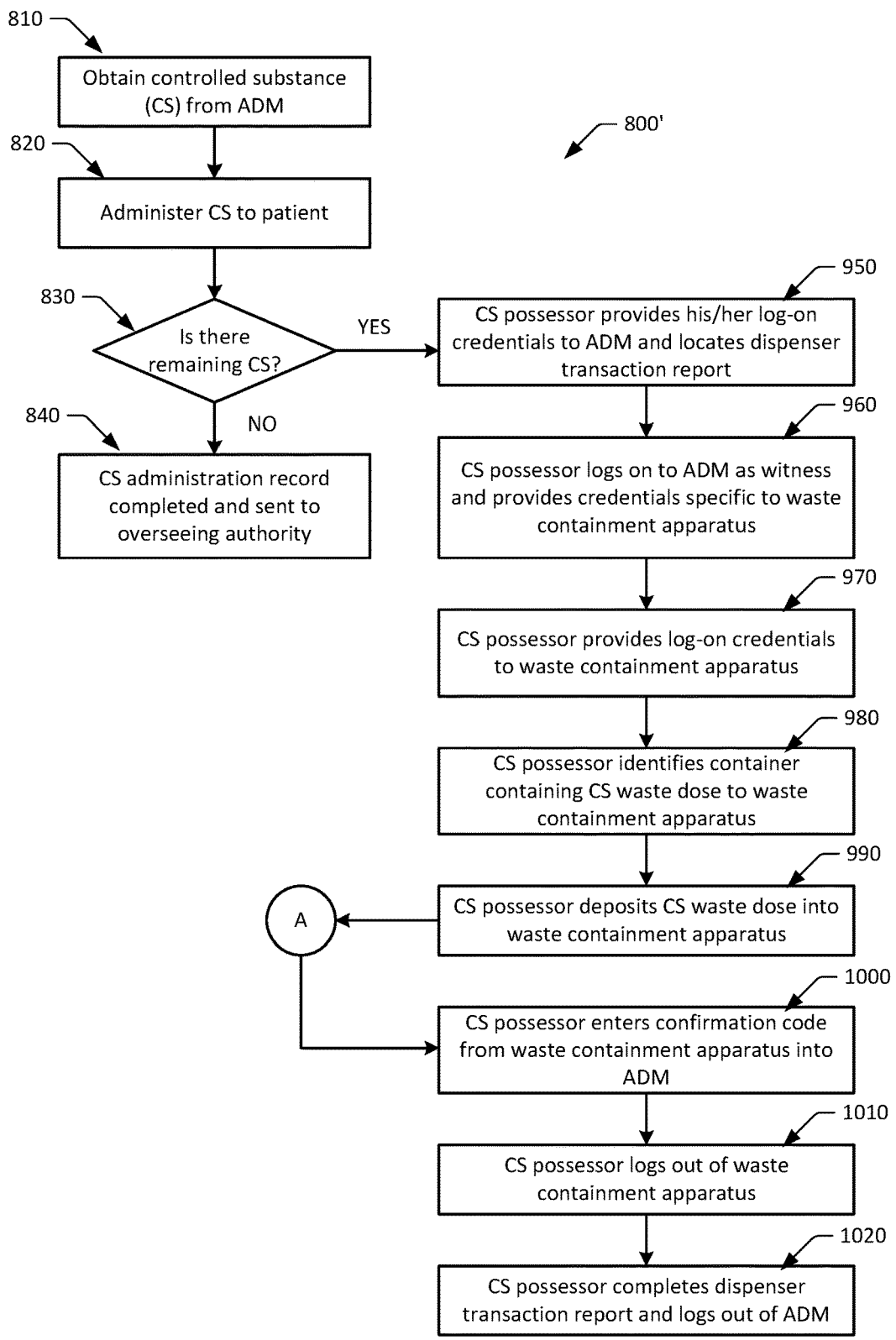
FIG. 19 is a flowchart diagram illustrating one embodiment of an improved waste procedure using the waste containment apparatus illustrated in FIG. 1.

The flowchart in FIG. 19 illustrates a new drug wastage procedure 800' for the disposal of controlled substances, which improves upon the procedure 800 shown in FIG. 18. In some embodiments, procedure 800' may begin similar to procedure 800, in that a controlled substance may be obtained in step 810 and administered to a patient in step 820. If there is no excess controlled substance remaining in step 830, the controlled substance possessor may complete the required controlled substance administration record and return the record to the pharmacy or overseeing authority 190 in step 840. If there is an excess of controlled substance (YES branch of step 830), the possessor must dispose of the excess substance (i.e., the CS waste dose) and document the disposal, but unlike the process 800 shown in FIG. 18, may do so without the assistance of a qualified witness.

In step 950, the possessor who originally obtained and administered the controlled substance provides log-on credentials to the ADM 180 and locates the dispenser transaction report 750 associated with the current waste transaction. No human witness is present. In lieu of a witness, the same possessor logs on to the ADM 180 again, this time as the witness using separate credentials specific to the waste containment apparatus 110 in step 960.

In step 970, the possessor provides log-on credentials to the waste containment apparatus 110 (e.g., via a finger swipe or scan, password entry via a touch screen, etc.) and creates a new waste transaction record in the apparatus 110. A unique transaction number is automatically assigned to this record by the apparatus 110 when it is created. As noted above, this transaction number may be based on the unique bar coded serial number of the cuvette 144, which will receive this specific dose. In step 980, the possessor identifies the container (e.g., the vial, syringe, etc.) originally or currently containing the CS waste dose to the waste containment apparatus 110. As noted above, the container may be identified in step 980 by scanning a barcode on the container (see, e.g., FIG. 3) to automatically enter the NDC number, drug type, concentration and original volume/quantity of the controlled substance prior to administration into the waste transaction record. In some embodiments, this information may be entered manually, e.g., using pull-down menus on a touch-screen interface to ensure the transaction can be properly completed in the event the bar code is not readable. It is noted, however, that no patient data or HIPAA-regulated data is entered into the apparatus 110 in step 980.

In step 990, the possessor deposits the CS waste dose into the waste containment apparatus 110 to securely contain the waste dose therein. As noted above and shown in FIGS. 9 and 10, the CS waste dose may be deposited into the apparatus 110 by injecting the dose into a waste input port (512, 612) on the apparatus 110. Once injected, the CS waste dose is secured within the waste containment apparatus 110 and the apparatus will perform the method steps shown in FIG. 4 and provide a confirmation code to the possessor. This code may be identical to the transaction number, and specific to the bar coded serial number of the cuvette into which this specific dose was deposited.

In step 1000, the possessor enters the confirmation code from the waste containment apparatus 110 in the ADM 180. In one embodiment, the possessor may enter the confirmation code in a comments section of the dispenser transaction report 750, either by manually keying it in or by scanning a barcode displayed on the display screen of the apparatus 110 using a handheld scanner on the ADM 180. In step 1010, the possessor logs out of the waste containment apparatus 110. In step 1020, the possessor completes the dispenser transaction report 750 and logs out of the ADM 180. The waste transaction is now complete and the possessor can move on to his/her other duties.

In the proposed drug wastage procedure 800' shown in FIG. 19, the waste containment apparatus 110 replaces the human witness required in the current drug wastage procedure 800. This provides a more efficient and accurate verification process, while providing a 50% reduction in labor. Since the waste containment apparatus 110 automatically verifies the deposited volume/quantity, as well as the composition and concentration of the CS waste dose when equipped with the optional on-board analyzer 150, the proposed drug wastage procedure 800' eliminates or at least reduces the opportunity for drug diversion and theft. The proposed drug wastage procedure 800' also enables full compliance with the CSA of 1970, the new DEA rules and state laws by securing each CS waste dose in a single-dose container, providing an exact count or measure of the contents in each container, rendering the contents of the container unsuitable for human use if measurement/analysis results indicate that the contents are what they are supposed to be, and generating all regulatory documentation required by state and federal laws for tracking and verifying the disposal of controlled substances.

In addition, the controlled substance waste tracking and disposal system 100, which includes the waste containment apparatus 110 and the tracking and reporting system 120 shown in FIG. 1, integrates easily into the waste operations of the hospital or other patient-care facility. Furthermore, the controlled substance waste tracking and disposal system 100 ensures that proper HIPAA protections are maintained at all times. The waste containment apparatus 110 and all of its data will be completely isolated from all hospital information systems, and will rely on manual input of data, for example, by finger swipe or bar code scan. No patient-specific information will be entered, stored, or accessed by the waste containment apparatus 110. It will also be password/biometrically secured and physically secured to discourage theft of the entire apparatus.

Figure 20:
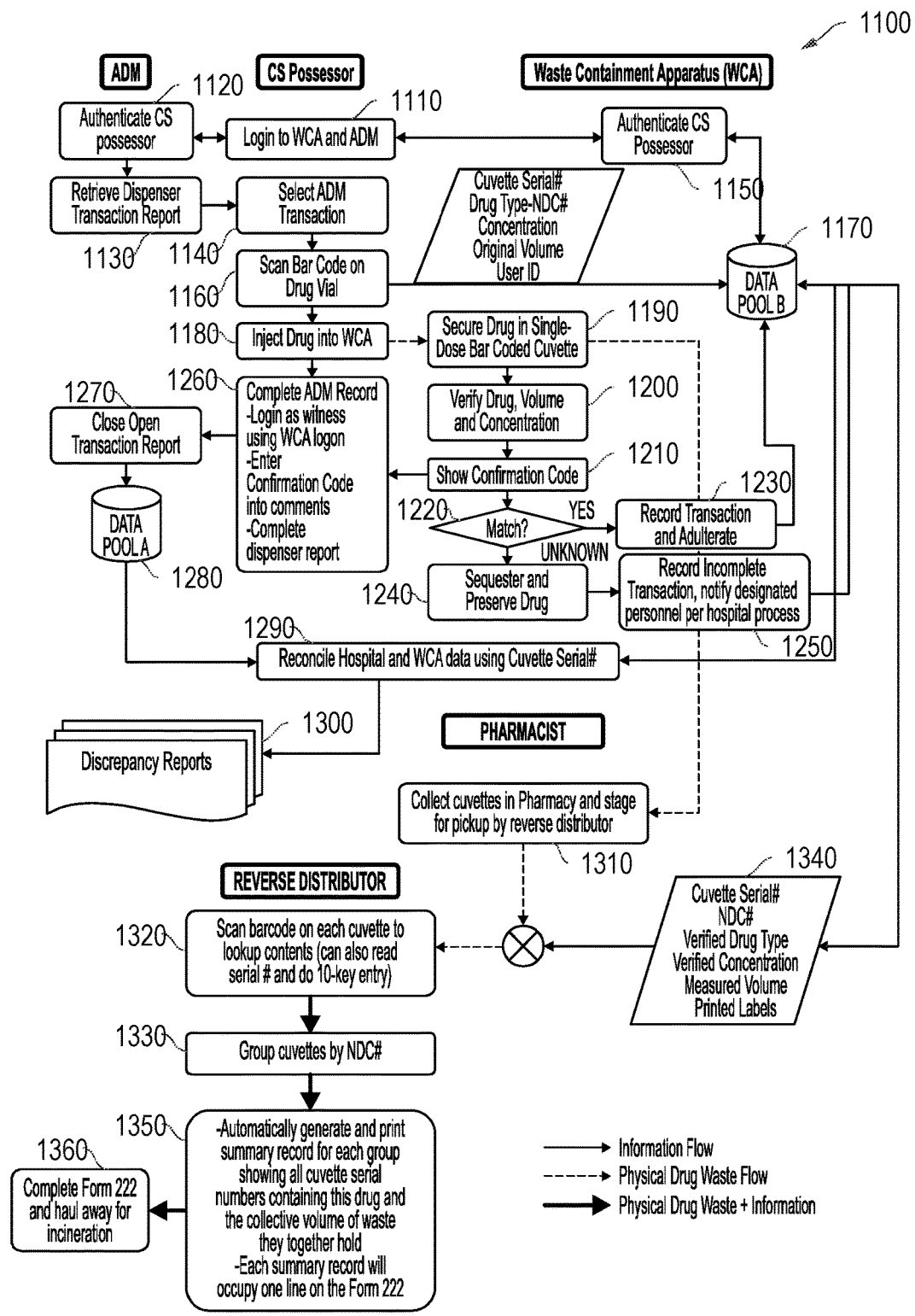
FIG. 20 is a process flowchart diagram illustrating the physical drug waste flow and the information flow between a CS possessor, ADM, waste containment apparatus, record keeping authority and reverse distributor, according to one embodiment.

FIG. 20 is a process flowchart diagram 1100 illustrating the physical drug waste flow and the information flow between a CS possessor, the ADM 180, the waste containment apparatus (WCA) 110, the record keeping authority 210 and the reverse distributor, according to one embodiment. As such, FIG. 20 illustrates how the controlled substance waste tracking and disposal system 100 of FIG. 1 integrates easily into the waste operations of a hospital or other patient-care facility, maintains HIPAA compliance, improves efficiency of the waste disposal process and meets all regulatory requirements for the tracking and verifying the disposal of controlled substances.

As noted above, the waste procedure may generally begin after a controlled substance is administered to a patient and a portion of the controlled substance remains. In order to properly dispose of the remaining substance (i.e., the CS waste dose), the controlled substance possessor logs on to the ADM from which the controlled substance was obtained and the waste containment apparatus at which the CS waste dose will be disposed (step 1110). After the ADM authenticates the possessor (step 1120), the ADM retrieves the possessor's open dispenser transaction reports (step 1130) and the possessor selects the dispenser transaction report corresponding to the current transaction (step 1140). After the WCA authenticates the possessor (step 1150), the possessor identifies the container containing the controlled substance (step 1160, e.g., by scanning the bar code on the drug vial or syringe) to enter information pertaining to the possessor and the controlled substance into data pool B (step 1170, e.g., information reconciler and recorder 160 and/or tracking and reporting system 120). The possessor then deposits the CS waste dose into the WCA (step 1180, e.g., by injecting the drug into the waste input port of the WCA).

Once deposited (step 1180), the CS waste dose is secured within a single-dose, bar-coded cuvette (step 1190), the volume/quantity, composition and concentration of the CS waste dose is analyzed and verified (step 1200) and a confirmation code is displayed (step 1210) by the WCA. If the analysis results from step 1200 match the information provided in step 1160 (YES branch of step 1220), a waste transaction record is recorded in data pool B (step 1170) and the CS waste dose is adulterated, rendered unusable for human consumption and/or rendered irretrievable (step 1230).

In some embodiments, an agent may be added to the CS waste dose contained within the cuvette 144 (step 1230) to denature, adulterate, destroy, neutralize and/or disinfect the controlled substance, as described above in reference to FIGS. 7-9. In other embodiments, the cuvette contents may be deposited within a waste storage bin where the contents may be rendered non-infectious, unusable, and/or irretrievable (step 1230) by addition of an agent and/or an absorbent material into an interior of the waste storage bin, as described above in reference to FIGS. 10-11. In some cases, such agents and/or absorbent materials may also convert the waste storage bin contents into a form, which is suitable for non-regulated waste disposal. In such cases, the waste storage bin may be disposed in the trash and the reverse distributor (described below) may be omitted from the waste disposal process.

If the analysis results from step 1200 do not match the information entered in step 1160 (UNKNOWN branch of step 1220), the CS waste dose is sequestered and preserved in the cuvette in which it was deposited (step 1240), an incomplete waste transaction record is recorded in data pool B and designated personnel are notified per hospital processes (step 1250). It is noted that steps 1190-1250 are performed automatically and independently by the WCA, and require no further input or action on the part of the controlled substance possessor.

Once the confirmation code is displayed by the WCA (step 1210), the possessor completes the dispenser transaction report 750 (step 1260), e.g., by logging in as the witness using the WCA log-on credentials, entering the confirmation code generated in step 1210 in the comments section, completing the dispenser transaction report, and logging out of the ADM, as noted above in FIG. 19. The ADM closes the open dispenser transaction report 750 (step 1270) and sends the report to data pool A (step 1280 (e.g., the data storage unit 200 of OAIS 190)).

Sometime thereafter, the record keeping authority (e.g., pharmacist) reconciles the waste transaction records stored within data pool B with the hospital records stored within data pool A (step 1290) and generates discrepancy reports (step 1300). The reconciliation process may be similar to that described above in FIG. 17. As noted above, proper HIPAA protections are maintained at all times, since only the record keeping authority has access to the dispenser transaction reports 750 (which may include patient-specific data). Furthermore, information flow from the WCA, to the data pool B (e.g., tracking and reporting system 120), to the record keeping authority running the reconciliation application is one-way only, and never in the other direction.

As noted above, the CS waste dose deposited within the single-dose, bar-coded cuvette 144 may remain within the cuvette, in some embodiments, as discussed above with regard to FIGS. 7-9. Once removed from the waste containment apparatus 110, cuvettes containing CS waste doses may be stored within a locked bin in the pharmacy until they are picked up by a reverse distributor for proper waste disposal in accordance with waste disposal regulations. The following description of steps 1310-1360 of FIG. 20 assumes that the CS waste doses remain within the cuvettes 144 for eventual pick up by the reverse distributor.

Once deposited (step 1180) and secured within a single-dose, bar-coded cuvette (step 1190), the CS waste dose remains secured until the cuvettes within the WCA are collected by the record keeping authority and staged for pickup by a reverse distributor (step 1310). As noted above with respect to FIG. 16, the reverse distributer may scan the barcode on each cuvette to lookup the contents contained therein (step 1320), group the cuvettes by NDC number (step 1330) and place each group within a different bag of waste.

In some embodiments, the reverse distributor may be given access to data pool B (e.g., tracking and reporting system 120) to simplify the documentation and chain of custody verification (step 1340). For example, information from data pool B may be used to generate and print out labels to clearly identify the bags of waste for each specific NDC number. As shown in FIG. 16, these labels 720 may identify the bag 710 contents by specifying the NDC number, the serial numbers of the cuvettes included within the bag, and the verified composition, concentration and volume of waste contained therein. Using such information, the reverse distributer can automatically generate and print a summary record for each group showing all cuvette serial numbers containing a particular drug and the collective volume of waste held within these cuvettes (step 1350). Each summary record will occupy one line on the Form 222, as shown in FIG. 16. After completing Form 222, the bagged and labeled cuvettes may be hauled away by the reverse distributer for proper waste disposal in accordance with waste disposal regulations (e.g., incineration) (step 1360).

It is noted, however, that a reverse distributor may not be needed for proper waste disposal in all embodiments. In the waste storage apparatus 600 shown in FIGS. 10-11, for example, the cuvette contents are deposited within a waste storage bin 690, and are rendered unusable for human consumption and/or irretrievable (e.g., converted into a solid form) by the addition of an agent and/or absorbent material. If such agents and/or absorbent materials convert the waste storage bin contents into a form, which is suitable for non-regulated waste disposal, the waste storage bin may simply be deposited in the trash. In this case, the reverse distributor may be removed from the waste disposal process shown in FIG. 20 and steps 1310-1360 may be omitted.

Advantages to the system, apparatus and methods described herein include, but are not limited to, eliminating the potential for a person to substitute any other clear liquid for a controlled substance, eliminating the need for a second medical professional to witness the disposal event, reducing the time required to dispose of controlled substances, expediting the review and reconciliation of the controlled substance transaction, eliminating the possibility for a person to illegally acquire medications that have been disposed, ensuring that all regulatory requirements for proper disposal and documentation of controlled substances is met, and ensuring that patient-specific data is protected under HIPAA guidelines.

While the system, apparatus and methods described herein may be adapted to various modifications and alternative forms, specific embodiments have been shown by way of example and described herein. However, it should be understood that the disclosure provided herein is not intended to be limited to only the particular forms disclosed. Rather, the disclosure is intended to cover all modifications, equivalents and alternatives falling within the spirit and scope of the disclosure as defined by the appended claims. Moreover, the different aspects of the disclosed system, apparatus and methods may be utilized in various combinations and/or independently and method steps may be performed in any order. Thus, the disclosure and claims are not limited to only those combinations shown herein, but rather may include other combinations.

What is claimed:

1. A waste containment apparatus, comprising:
    a plurality of single-dose containers each configured for receiving a controlled substance waste dose, wherein each single-dose container comprises:
        an inlet port for receiving a controlled substance waste dose;
        an analysis chamber coupled to the inlet port for receiving and reserving a fixed amount of the received controlled substance waste dose for analysis; and
        a storage chamber coupled to the analysis chamber for receiving and storing a remaining portion of the received controlled substance waste dose.

2. The waste containment apparatus as recited in claim 1, wherein each single-dose container further comprises a spillway arranged near a top of the analysis chamber to provide an outlet for the remaining portion of the received controlled substance waste dose to spill over into the storage chamber.

3. The waste containment apparatus as recited in claim 1, wherein the analysis chamber is configured for reserving about 0.1 ml to about 2 ml of the received controlled substance waste dose, and wherein the storage chamber is configured for storing about 5 ml to about 20 ml of the received controlled substance waste dose.

4. The waste containment apparatus as recited in claim 1, wherein each single-dose container further comprises a second inlet port for receiving another substance into at least one of the analysis chamber and the storage chamber.

5. The waste containment apparatus as recited in claim 4, wherein each single-dose container further comprises a cap, which when closed, is configured for engaging with and sealing at least one of the first inlet port and the second inlet port.

6. The waste containment apparatus as recited in claim 1, wherein at least one of the analysis chamber and the storage chamber comprises an optically transmissive material.

7. The waste containment apparatus as recited in claim 1, further comprising a laser level, a camera or a flowmeter coupled to detect an amount or a volume of the controlled substance waste dose received within the single-dose container.

8. The waste containment apparatus as recited in claim 1, further comprising an analyzer coupled to the analysis chamber, wherein the analyzer is configured for determining a composition and/or concentration of the controlled substance waste dose reserved within the analysis chamber.

9. The waste containment apparatus as recited in claim 8, wherein the analyzer is configured for determining the composition and/or concentration of the controlled substance waste dose using a Rayleigh scattering or a Raman spectroscopy technique.

10. The waste containment apparatus as recited in claim 8, wherein the analyzer is configured for measuring a volume of the controlled substance waste dose received within the single-dose container.

11. The waste containment apparatus as recited in claim 8, further comprising:
  one or more input devices configured for receiving, from a depositor of the controlled substance waste dose, information pertaining to the controlled substance waste dose deposited into the waste containment apparatus and received within each single-dose container; and
  an information reconciler and recorder securely disposed within a housing of the waste containment apparatus and coupled for comparing the composition, the concentration and/or a volume of the controlled substance waste dose identified by the analyzer to the information received via the one or more input devices to determine if a match exists, and for producing a comparison result indicative of a confirmed match or an unconfirmed match based on said comparing.

12. A method for receiving, analyzing, verifying and disposing of a controlled substance waste dose, the method comprising:
  receiving a controlled substance waste dose deposited within a single-dose container securely disposed within a waste containment apparatus;
  measuring a volume of the controlled substance waste dose deposited within the single-dose container;
  determining a composition and concentration of the controlled substance waste dose deposited within the single-dose container;
  comparing the volume, the composition and the concentration of the controlled substance waste to information pertaining to the controlled substance waste dose, wherein the information is received, via an input device of the waste containment apparatus, from a depositor of the controlled substance waste dose; and
  verifying the controlled substance waste dose deposited within the single-dose container if said comparing step determines that the volume, composition and concentration of the controlled substance waste matches the received information pertaining to the controlled substance waste dose.

13. The method as recited in claim 12, further comprising receiving the information pertaining to the controlled substance waste dose, wherein the received information comprises one or more of a National Drug Code (NDC) number, a drug type, a concentration and an original volume of the controlled substance prior to administration to a patient.

14. The method as recited in claim 13, wherein said receiving the information comprises scanning a barcode on a container originally containing the controlled substance waste dose to obtain the information pertaining to the controlled substance waste dose.

15. The method as recited in claim 12, wherein said measuring a volume comprises measuring the volume of the controlled substance waste dose deposited within the single-dose container using a laser level, a weight measurement, a camera site level reading or a flowmeter.

16. The method as recited in claim 12, wherein said determining a composition and concentration comprises determining the composition and concentration of the controlled substance waste dose deposited within the single-dose container using a Rayleigh scattering or a Raman spectroscopy technique.

17. The method as recited in claim 12, wherein if said comparing step determines that the volume, composition and/or concentration of the controlled substance waste dose does not match the received information pertaining to the controlled substance waste dose, the method further comprises sequestering the controlled substance waste dose within the single-dose container in its original form.

18. The method as recited in claim 12, wherein if said comparing step determines that the volume, composition and/or concentration of the controlled substance waste dose matches the received information pertaining to the controlled substance waste dose, the method further comprises rendering the controlled substance waste dose unusable for human consumption by adding an agent and/or an absorbent material to the controlled substance waste dose deposited within a single-dose container.

19. The method as recited in claim 12, wherein if said comparing step determines that the volume, composition and concentration of the controlled substance waste dose matches the received information pertaining to the controlled substance waste dose, the method further comprises:
  depositing the controlled substance waste dose into a waste storage bin securely disposed within the waste containment apparatus; and
  introducing an absorbent material into the waste storage bin after the controlled substance waste dose is deposited into the waste storage bin to render the controlled substance waste dose unusable, irretrievable and/or in a form suitable for non-regulated waste disposal.

20. The method as recited in claim 19, wherein the absorbent material is introduced into the waste storage bin after the controlled substance waste dose is deposited into the waste storage bin or after multiple controlled substance waste doses from a plurality of single-dose containers are deposited into the waste storage bin.

* * * * *